US006744706B2

(12) United States Patent
Miyagawa et al.

(10) Patent No.: US 6,744,706 B2
(45) Date of Patent: Jun. 1, 2004

(54) OPTICAL SYSTEM WITH TRACKING CONTROLLER

(75) Inventors: Naoyasu Miyagawa, Kawanishi (JP); Yasuhiro Gotoh, Kadoma (JP); Tetsuya Akiyama, Hirakata (JP)

(73) Assignee: Matsushita Electric Industrial Co., Kadoma (JP)

(*) Notice: Subject to any disclaimer, the term of this patent is extended or adjusted under 35 U.S.C. 154(b) by 0 days.

(21) Appl. No.: 10/260,672

(22) Filed: Sep. 30, 2002

(65) Prior Publication Data

US 2003/0058757 A1 Mar. 27, 2003

Related U.S. Application Data

(62) Division of application No. 10/056,129, filed on Jan. 25, 2002, now Pat. No. 6,487,147, which is a division of application No. 09/607,426, filed on Jun. 27, 2000, now abandoned, which is a division of application No. 08/674,583, filed on Jul. 2, 1996, now Pat. No. 6,118,752.

(30) Foreign Application Priority Data

Jul. 7, 1995 (JP) .............................................. 7-171828
Sep. 21, 1995 (JP) .............................................. 7-243496

(51) Int. Cl.$^7$ .............................................. G11B 7/095
(52) U.S. Cl. ................................ 369/44.13; 369/44.34; 369/275.4; 369/44.26
(58) Field of Search ........................... 369/44.13, 44.26, 369/44.34, 44.35, 47.22, 47.35, 275.3–275.4

(56) References Cited

U.S. PATENT DOCUMENTS

| | | | |
|---|---|---|---|
| 4,223,347 A | 9/1980 | Bouwhuis et al. | |
| 4,707,816 A | 11/1987 | Yonezawa et al. | |
| 4,748,609 A | 5/1988 | Yonezawa et al. | |
| 4,967,403 A | 10/1990 | Ogawa et al. | |
| 4,980,877 A | 12/1990 | Sugiyama et al. | |
| 5,031,166 A | 7/1991 | Getreuer et al. | |
| 5,270,991 A | 12/1993 | Verboom | |
| 5,404,345 A | 4/1995 | Taki | |
| 5,448,551 A | 9/1995 | Miyagawa et al. | |
| 5,452,284 A | 9/1995 | Miyagawa et al. | |
| 5,508,995 A | 4/1996 | Moriya et al. | |
| 5,537,373 A | 7/1996 | Horikiri | |
| 6,118,752 A | * 9/2000 | Miyagawa et al. | 369/275.3 |
| 6,487,147 B2 | * 11/2002 | Miyagawa et al. | 369/44.26 |

FOREIGN PATENT DOCUMENTS

| | | |
|---|---|---|
| EP | 0588305 | 3/1994 |
| EP | 07014172 | 1/1995 |
| JP | 5068413 | 6/1975 |
| JP | 61224145 | 10/1986 |
| JP | 6357859 | 11/1988 |
| JP | 5282705 | 10/1993 |
| JP | 6176404 | 6/1994 |
| JP | 6338064 | 12/1994 |
| JP | 7-50014 | 2/1995 |

\* cited by examiner

Primary Examiner—W. R. Young
(74) Attorney, Agent, or Firm—Renner, Otto, Boisselle & Sklar, LLP

(57) ABSTRACT

An optical information recording medium according to the present invention includes at least one groove track and at least one land track allowing information to be recorded on or reproduced from the groove track and the land track, the groove track and the land track adjoining each other. The optical information recording medium further includes: an identification signal region including a pre-pit array, the pre-pit array indicating identification information concerning the groove track and the land track; and a servo control region disposed ahead of the identification signal region along the groove track and the land track, the servo control region including wobble pits positioned so as to shift to opposite sides of a center line of either the groove track or the land track.

1 Claim, 22 Drawing Sheets

OPTICAL SYSTEM WITH TRACKING CONTROLLER

This is a division of application Ser. No. 10/056,129, filed Jan. 25, 2002 and now U.S. Pat. No. 6,487,147, which was a division of application Ser. No. 09/607,426 filed Jun. 27, 2000 and now abandoned, which was a division of application Ser. No. 08/674,583 file date Jul. 2, 1996 now U.S. Pat. No. 6,118,752.

BACKGROUND OF THE INVENTION

1. Field of the Invention

The present invention relates to: an optical information recording medium which utilizes both groove regions (i.e., guide grooves) and land regions (i.e., regions between grooves) as information tracks, the grooves and lands having been previously formed on the optical information recording medium; and an optical information recording/reproduction device for recording an information signal on the optical information recording medium.

2. Description of the Related Art

In recent years, there have been vigorous research and development activities for realizing optical information recording media for recording and reproducing information signals (e.g., video signals and audio signals) thereon. One example of such an optical information recording medium is an optical disk. A recordable optical disk includes guide grooves (hereinafter referred to as "grooves") previously engraved on a substrate, the grooves constituting information tracks. Any region between adjoining grooves is referred to as a "land". Information signals can be recorded or reproduced on the optical disk by converging a laser light beam on the flat portions of grooves or lands.

In the case of common commercially-available optical disks, information signals are typically recorded on either grooves or lands. When information signals are recorded on the grooves, for example, the lands serve as guard bands for separating adjoining tracks defined by the grooves. In the case where information signals are recorded on the lands, the grooves serve as guard bands.

FIG. 9 is a magnified perspective view of a conventional optical disk having the above-mentioned structure. In FIG. 9, reference numeral 85 denotes a recording layer (which may be composed of a phase-change material, for example); 86 denotes a recording pit; 87 denotes a laser beam spot; 88, 90, and 92 denote guide grooves defining "grooves"; 89 and 91 denote "lands"; 93 denotes a transparent substrate through which light enters. As seen from FIG. 9, grooves are made wider than lands in this exemplary conventional optical disk.

In an attempt to increase the recording capacity of the above conventional optical disk, the interspaces between tracks are shortened by narrowing the widths of the lands 89. However, a smaller interspace between tracks results in a larger diffraction angle of light reflected from the grooves. This results in a lower level of tracking error signal, which is employed to ensure accurate tracing of the beam spot 87 on the tracks.

Moreover, there is a limit to the increase in track density achieved by merely reducing land widths. However, reducing the groove widths might lower the amplitude of the reproduced signal due to thinner recording pits 86.

On the other hand, there are techniques for increasing the track density, such as that disclosed in Japanese Patent Publication No. 63-57859, according to which information signals are recorded on both grooves and lands.

FIG. 10 is a magnified perspective view of such an optical disk. In FIG. 10, reference numeral 85 denotes a recording layer; 86 denotes a recording pit; 87 denotes a laser beam spot; 93 denotes a transparent substrate; 94, 96, and 98 denote grooves; 95 and 97 denote lands.

As shown in FIG. 10, the grooves and the lands have substantially the same width. Pre-pits 99, which are formed for both grooves and lands, are engraved at the beginnings of sectors of both information tracks (i.e., groove and lands) as identification signals representing locational information on the optical disk.

In the above optical disk, the recording pits 86 are formed for both grooves and lands as shown in FIG. 10. Although the grooves have a period equal to the period of grooves in the optical disk shown in FIG. 9, each interspace between adjoining recording pit rows in FIG. 10 is half of that of the optical disk shown in FIG. 9. As a result, the optical disk in FIG. 10 has twice as large a recording capacity as that of the optical disk in FIG. 9.

Rewritable optical disks require identification signals (indicating location information on the disk), etc., to be previously recorded on the disk. The inventors of the present invention have proposed in Japanese Laid-Open Patent Publication No. 6-176404 a technique of recording one identification signal for an adjoining pair consisting of a groove and a land so as to be located between the groove and the land.

However, in the above-mentioned optical information recording media, the track pitch is reduced to half of that of conventional optical information recording media, thereby requiring an even more accurate track servo control. Particularly when an identification signal is recorded between a land and its corresponding groove, only one half of the beam spot will be incident on the pre-pits. Therefore, when the beam spot shifts away from the track center, toward regions where the identification signal is not present, it may be impossible to detect the identification signal.

SUMMARY OF THE INVENTION

An optical information recording medium according to the present invention includes at least one groove track and at least one land track allowing information to be recorded on or reproduced from the groove track and the land track, the groove track and the land track adjoining each other, wherein the optical information recording medium further includes: an identification signal region including a pre-pit array, the pre-pit array indicating identification information concerning the groove track and the land track; and a servo control region disposed ahead of the identification signal region along the groove track and the land track, the servo control region including wobble pits positioned so as to shift to opposite sides of a center line of either the groove track or the land track.

In one embodiment of the invention, the wobble pits include a plurality of pairs of pre-pits positioned so as to shift to opposite sides of the center line.

In another embodiment of the invention, the plurality of pairs of pre-pits indicate a reproduction synchronization signal.

In still another embodiment of the invention, a synchronization signal section indicating the beginning of the wobble pits is provided immediately before the wobble pits, and the synchronization signal section includes a pit array positioned on the center line of either the groove track or the land track.

In still another embodiment of the invention, at least a portion of the pre-pit array in the identification signal region is formed so as to be shifted away from the center line of either the groove track or the land track.

In still another embodiment of the invention, the identification signal region includes a pit indicating a track identification signal.

In still another embodiment of the invention, the pit indicating the track identification signal is shifted away from the center line of either the groove track or the land track.

In still another embodiment of the invention, the groove track and the land track are divided into a plurality of sectors, the pre-pit array in the identification signal region includes an address pit array indicating address information of a corresponding sector.

In still another embodiment of the invention, the groove track and the land track are formed in a spiral or concentric shape on a disk substrate.

In still another embodiment of the invention, the identification information includes a track number.

In still another embodiment of the invention, a portion of the pre-pit array indicating the identification signal that indicates the track number is shifted away from the center line of either the groove track or the land track along a direction across the groove track and the land track.

In still another embodiment of the invention, pre-pits in the pre-pit array indicating the identification signal which are formed so as to be shifted away from the center line of either the groove track or the land track are shifted away from the center line of either the groove track or the land track by about ¼ of a track pitch.

In still another embodiment of the invention, an optical depth or height of the pre-pit array indicating the identification signal is substantially equal to the depth of the groove track.

In still another embodiment of the invention, an optical depth or height of the pre-pit array indicating the identification signal is substantially equal to $\lambda/4$ (where $\lambda$ represents the wavelength of a light beam)

In still another embodiment of the invention, the width of the pre-pit array indicating the identification signal is substantially equal to the width of the groove track.

In still another embodiment of the invention, the width of the pre-pit array in the synchronization signal or the pre-pit array indicating the identification signal is larger than the width of the groove track.

In still another embodiment of the invention, a gap section is provided between the servo control region and the identification signal region.

In still another embodiment of the invention, the optical information recording medium further includes a rewritable recording layer, wherein the recording layer is formed of a phase-change type material capable of taking an amorphous state or a crystal state.

In another aspect, the present invention provides an optical information recording/reproduction device for recording/reproducing information with a light beam on an optical information recording medium including at least one groove track and at least one land track allowing information to be recorded on or reproduced from the groove track and the land track, the groove track and the land track adjoining each other, and the optical information recording medium further including: an identification signal region including a pre-pit array, the pre-pit array indicating identification information concerning the groove track and the land track; and a servo control region disposed ahead of the identification signal region along the groove track and the land track, the servo control region including wobble pits positioned so as to shift to opposite sides of a center line of either the groove track or the land track, and the optical information recording/reproduction device including: an optical system for allowing the light beam emitted from a light source to be incident on the optical information recording medium; transportation means for moving the relative position of a light spot on the optical information recording medium created by the light beam along a direction in which the groove track and the land track extend; light detection means for receiving reflected light of the beam spot from the optical information recording medium in a plurality of light receiving portions and for converting the reflected light into an electric signal which is output as a light detection signal; identification signal reading means for reproducing the identification signal from the light detection signal; a first tracking error detection circuit for detecting, while the optical spot travels on the groove track or the land track, a shift amount of the optical spot with respect to the center line and for outputting a first error signal indicating the shift amount; a second tracking error detection circuit for detecting, while the optical spot is travelling over the servo control region, a shift amount of the optical spot with respect to the center line by detecting the intensity of returned light from the wobble pits and for outputting a second error signal indicating the shift amount; a correction circuit for outputting a tracking signal obtained by correcting the first error signal based on the second error signal; and a tracking controller for controlling the transportation means to cause the beam spot to travel over the groove track or the land track based on the tracking signal.

Alternatively, the present invention provides an optical information recording/reproduction device for recording/reproducing information with a light beam on an optical information recording medium including at least one groove track and at least one land track allowing information to be recorded on or reproduced from the groove track and the land track, the groove track and the land track adjoining each other, and the optical information recording medium further including: an identification signal region including a pre-pit array, the pre-pit array indicating identification information concerning the groove track and the land track; and a servo control region disposed ahead of the identification signal region along the groove track and the land track, the servo control region including wobble pits positioned so as to shift to opposite sides of a center line of either the groove track or the land track; and a synchronization signal section indicating the beginning of the wobble pits, the synchronization signal section being provided immediately before the wobble pits and including a pit array positioned on the center line of either the groove track or the land track, and the optical information recording/reproduction device including: an optical system for allowing the light beam emitted from a light source to be incident on the optical information recording medium; transportation means for moving the relative position of a light spot on the optical information recording medium created by the light beam along a direction in which the groove track and the land track extend; light detection means for receiving reflected light of the beam spot from the optical information recording medium in a plurality of light receiving portions and for converting the reflected light into an electric signal which is output as a light detection signal; identification signal reading means for reproducing the identification signal from the light detection signal; a first tracking error detection circuit for detecting, while the optical spot travels on the groove track or the land track, a shift amount of the optical spot with respect to the center line and for outputting a first error signal indicating the shift amount; synchronization signal detection means for detecting from the light detection signal a point in time at which the beam spot travels over the synchronization signal section and outputting a reference signal indicating the point in time; a second tracking error detection circuit for detecting, while the optical spot is travelling over the servo control region, a shift amount of the optical spot with respect to the center line based on the reference signal and the light detection signal and for outputting a second error signal indicating the shift amount; synthesizing means for outputting a tracking signal based on the first error signal and the second error signal; and a tracking controller for controlling the transportation means to cause the beam spot to travel over the groove track or the land track based on the tracking signal.

In one embodiment of the invention, the synthesizing means outputs a signal obtained by adding the second error signal to the first error signal as the third error signal.

In another embodiment of the invention, the synthesizing means includes: identification signal region detection means for detecting whether or not the beam spot is travelling over the identification signal region and outputting a region detection signal while the beam spot is travelling over the identification signal region; and error signal retention means for retaining the third error signal while the region detection signal is output.

In still another embodiment of the invention, the second tracking error detection means derives a difference between a d.c. component of the light detection signal obtained after the lapse of a first time interval from a point in time at which the reference signal is input and a d.c. component of the light detection signal obtained after the lapse of a second time interval from the point in time and generates the second error signal based on the difference.

In still another embodiment of the invention, the light detection means includes two light receiving portions disposed symmetrically with respect to a direction across the groove track and the land track, each light receiving portion converting a received light amount into an electric signal; the first tracking error detection means includes differential operation means for deriving a difference between the electric signals output from the two light receiving portions; and the second tracking error detection means includes addition operation means for deriving a sum of the electric signals output from the two light receiving portions; and In still another embodiment of the invention, the optical information recording/reproduction device further includes: recording means for recording an information signal on the groove track or the land track; recording control means for controlling the recording means so as not to record the information signal in the identification signal region.

Alternatively, the present invention provides an optical information recording medium including at least one groove track and at least one land track allowing information to be recorded on or reproduced from the groove track and the land track, the groove track and the land track adjoining each other, wherein the optical information recording medium further includes: a pre-pit array indicating identification information concerning the groove track and the land track; and a plurality of pits disposed ahead of the pre-pit array along the groove track and the land track, the plurality of pits indicating a reproduction synchronization signal for reproducing the identification information of the pre-pit array, the plurality of pits indicating the reproduction synchronization signal being positioned so as to shift to opposite sides of a center line of either the groove track or the land track.

In one embodiment of the invention, the groove track and the land track are divided into a plurality of sectors, the pre-pit array in the identification signal region includes an address pit array indicating address information of a corresponding sector.

Alternatively, the present invention provides an optical information recording/reproduction device for recording/reproducing information with a light beam on an optical information recording medium including at least one groove track and at least one land track allowing information to be recorded on or reproduced from the groove track and the land track, the groove track and the land track adjoining each other, and the optical information recording medium further including: a pre-pit array indicating identification information concerning the groove track and the land track; and a plurality of pits disposed ahead of the pre-pit array along the groove track and the land track, the plurality of pits indicating a reproduction synchronization signal for reproducing the identification information of the pre-pit array, the plurality of pits indicating the reproduction synchronization signal being positioned so as to shift to opposite sides of a center line of either the groove track or the land track, wherein the optical information recording/reproduction device includes a circuit for correcting a tracking offset based on the plurality of pits indicating the reproduction synchronization signal.

Alternatively, the present invention provides an optical information recording medium including information tracks including at least one groove track and at least one land track formed in a spiral or concentric shape on a disk substrate, the optical information recording medium including at least one zone composed of a plurality of information tracks, wherein the optical information recording medium further includes: a servo control region defined by a meandering portion of the groove track, the meandering portion having at least one meander; an identification signal region including one pre-pit indicating an identification signal provided for a pair consisting of adjoining ones of the groove track and the land track, the center lines of some or all of the pre-pits being shifted away from the center line of either the groove track or the land track along a direction across the groove track and the land track; and an information signal region in which an information signal is recorded by irradiation of a light beam, the an information signal region being distinct from the identification signal region.

Alternatively, the present invention provides an optical information recording medium including at least one groove track and at least one land track allowing information to be recorded on or reproduced from the groove track and the land track, the groove track and the land track adjoining each other, the optical information recording medium further including: an identification signal region including a pre-pit array indicating identification information concerning the groove track and the land track; and an information signal region in which an information signal is recorded by irradiation of a light beam, wherein the pre-pit array indicating the identification signal includes: a field number pre-pit indicating a field number representing the order of information fields composed of a pair consisting of adjoining ones of the groove track and the land track; and a track identification pre-pit for detecting whether a beam spot created on the optical information recording medium by the light beam is currently travelling over the groove track or the land track, wherein the field number pre-pit is formed substantially on a border line between the groove track and the land track included in each information field, the field number pre-pit being provided with a period twice as large as a track pitch along a direction perpendicular to the groove track and the land track, and the track identification pre-pit is formed substantially on a border line between two adjoining information fields, the track identification pre-pit being provided with a period four as large as the track pitch along the direction perpendicular to the groove track and the land track.

In one embodiment of the invention, the track identification pre-pit includes: a first track identifier disposed on the same line as the field number pre-pit array; a second track identifier disposed ahead of the first track identifier along the track direction and located between the first track identifiers adjoining each other along the direction perpendicular to the groove track and the land track.

In another embodiment of the invention, the optical information recording medium further includes a rewritable recording layer, wherein the recording layer is formed of a phase-change type material capable of taking an amorphous state or a crystal state.

Alternatively, the present invention provides an optical information recording/reproduction device for recording/reproducing information with a light beam on an optical information recording medium including at least one groove track and at least one land track allowing information to be recorded on or reproduced from the groove track and the land track, the groove track and the land track adjoining each other, the optical information recording medium further including: an identification signal region including a pre-pit array indicating identification information concerning the groove track and the land track; and an information signal region in which an information signal is recorded by irradiation of a light beam, wherein the pre-pit array indicating the identification signal includes: a field number pre-pit indicating a field number representing the order of information fields composed of a pair consisting of adjoining ones of the groove track and the land track; and a track identification pre-pit for detecting whether a beam spot created on the optical information recording medium by the light beam is currently travelling over the groove track or the land track, wherein the field number pre-pit is formed substantially on a border line between the groove track and the land track included in each information field, the field number pre-pit being provided with a period twice as large as a track pitch along a direction perpendicular to the groove track and the land track, and the track identification pre-pit is formed substantially on a border line between two adjoining information fields, the track identification pre-pit being provided with a period four as large as the track pitch along the direction perpendicular to the groove track and the land track, wherein the optical information recording/reproduction device includes: an optical system for allowing the light beam emitted from a light source to be incident on the optical information recording medium; light detection means for receiving the light beam reflected from the optical information recording medium and converting the reflected light into an electric signal which is output as a light detection signal; identification signal reading means for reproducing the identification signal from the light detection signal and outputting at least the field number; and track identifier detection means for outputting an identifier detection signal in the case where a signal from the track identification pre-pit is detected.

Thus, the invention described herein makes possible the advantages of: (1) providing an optical information recording medium utilizing information tracks composed of grooves and lands previously formed on the optical information recording medium, which does not require an unduly high accuracy of track serve control; and (2) providing an optical information recording/reproduction device for recording an information signal on such an optical information recording medium.

These and other advantages of the present invention will become apparent to those skilled in the art upon reading and understanding the following detailed description with reference to the accompanying figures.

DESCRIPTION OF THE PREFERRED EMBODIMENTS

Hereinafter, the optical information recording medium and the optical information recording/reproduction device of the present invention will be described by way of examples, with reference to the accompanying figures.

In the examples described below, a recordable/reproducible optical disk will be illustrated which employs a phase-change type recording material (such that recording can be made based on changes in the reflection coefficient thereof). The examples will also be directed to a case where the angular velocity (CAV) method is employed as a method for controlling the rotation of the optical disk.

However, the present invention is applicable to any optical information recording medium which at least utilizes lands and grooves. For example, the optical information recording medium does not have to be of a reflection type but can also be a transmission type. Moreover, the present invention is applicable to recording media on which information can be recorded by optical means, e.g., those which are recordable by the phase-change method, the magnetooptical method, and the organic dye method.

EXAMPLE 1

Hereinafter, a first example of the present invention will be described with reference to FIG. 1.

Figure 1:
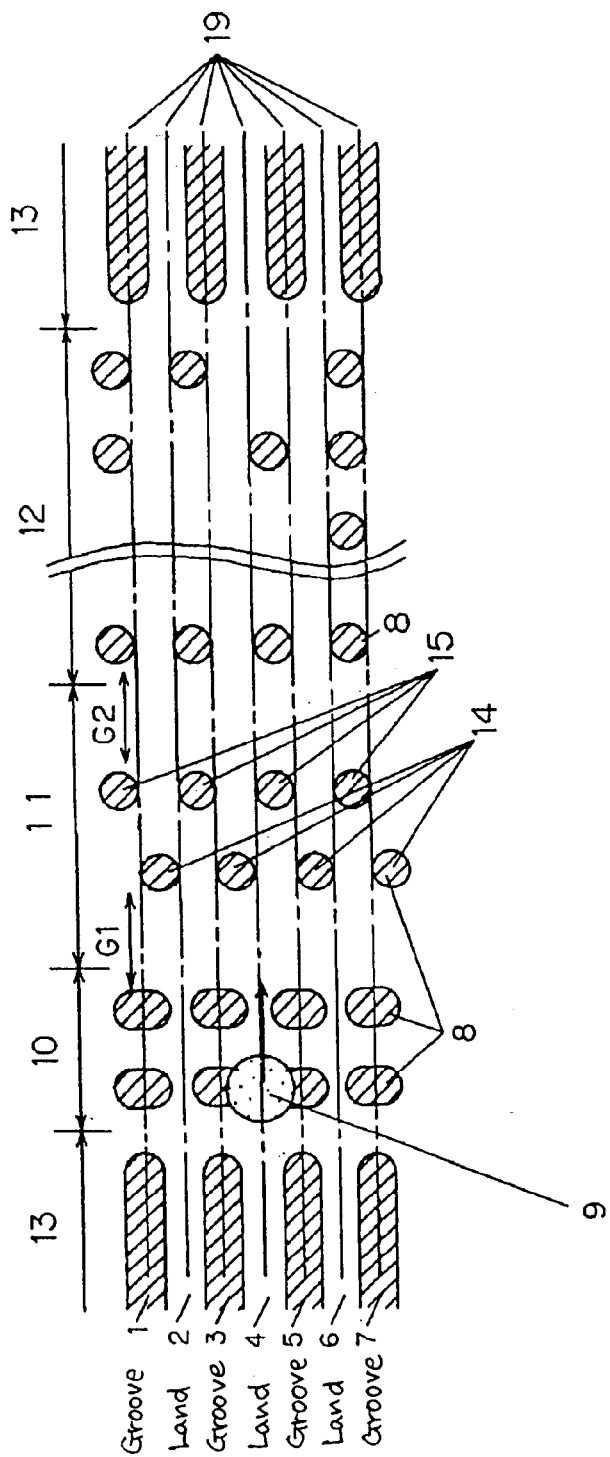
FIG. 1 is a magnified plan view showing an essential portion of the optical disk according to an example of the present invention.

FIG. 1 is a magnified plan view showing an essential portion of the optical disk according to the present example.

In FIG. 1, reference numerals 1, 3, 5, and 7 denote grooves; 2, 4, and 6 denote lands; 8 denotes a pre-pit; 9 denotes a beam spot. The lands and the grooves have substantially the same width.

A region 10 is defined as a synchronization signal section. No groove is formed within the region 10, but pre-pits are formed so as to be on imaginary extensions of the grooves. The pre-pits in the region 10 have a larger width than the other pre-pits in FIG. 1.

The pre-pits are formed to have a depth equal to the difference in height between the grooves and the lands. The depth of each groove can be prescribed at any value between about $\lambda/10$ and about $\lambda/4$ in terms of optical length (where $\lambda$ represents the wavelength of the laser light used for reading out information on the optical disk). In particular, the groove depth is preferably between about $\lambda/7$ and about $\lambda/5$ in order to reduce crosstalk occurring between adjoining tracks, as described in Japanese Laid-Open Patent Publication No. 5-282705.

A region 11 is defined as a wobble pit section. In this region, too, no groove is formed, but pre-pits are provided so as to wobble to the right/left and the front/back (along the tracing direction by the beam spot 9) with respect to a center line of each information track.

As shown in FIG. 1, the pre-pits form two discrete groups (14 and 15) regarding their positions along the longitudinal direction of the information tracks. Hereinafter, the pre-pits 14 which are to be traced earlier by the beam spot 9 traveling on the tracks in the direction of an arrow in FIG. 1 will be referred to as the "first wobble pits", and the pre-pits 15 which are to be traced later by the beam spot 9 than the first wobble pits will be referred to as the "second wobble pits".

The first wobble pits and the second wobble pits are shared by adjoining information tracks. Therefore, when the beam spot 9 traces a land, the first wobble pits 14 are situated on the left of the direction of the travel of the beam spot 9 (indicated by the arrow in FIG. 1). On the other hand, when the beam spot 9 traces a groove, the first wobble pits 14 are situated on the right of the direction of the travel of the beam spot 9.

Similarly, when the beam spot 9 traces a land, the second wobble pits 15 are situated on the right of the direction of the travel of the beam spot 9 (indicated by the arrow). On the other hand, when the beam spot 9 traces a groove, the second wobble pits 15 are situated on the left of the direction of the travel of the beam spot 9. Thus, a tracking error amount can be detected based on a difference between the amount of returned light obtained when the beam spot 9 is on the first wobble pits and the amount of returned light obtained when the beam spot 9 is on the second wobble pits. The principle of the tracking error amount detection is described in more detail in Japanese Laid-Open Patent Publication No. 61-224145, for example.

A region 12 is defined as an identification signal section. No groove is formed in the region 12. If at all, pre-pits representing identification signals are formed for every other track so as to be located between the center line of a groove and the center line of a land (the presence of such a pre-pit would indicate, for example, logical "1", whereas the absence of such a pre-pit would indicate, for example, logical "0"). The "identification signals" as used herein refer to various identification signals employed for a general optical information recording medium, such as track and/or sector locational information signals (indicating locations on the recording medium), sector marks, and reference synchronization signals.

When a beam spot passes over the identification signal section, a portion of the beam spot travels over the pre-pits for both lands and grooves. Therefore, the amount of reflected light is modulated by the pre-pit array. Thus, the identification signals can be reproduced for both lands and grooves.

A region 13 is defined as a main information signal section. As in conventional optical disks, recording pits are formed in the main information signal section in accordance with information signals of video, audio or computer data, etc. The dot-dash lines 19 indicate the respective center lines of grooves and lands. Gaps G1 and G2 are formed before and after the wobble pit section 11, respectively.

The wobble pit section 11 is located before the identification signal section 12, rather than immediately before the main information signal section 13. Thus, the tracking error signal correction (which is performed by utilizing the wobble pit section 11) is started before the tracking error signal begins to have disturbances due to the pre-pits of the identification signal section 12. As a result, the disturbance in the tracking error signal due to the pre-pits of the identification signal section 12 is minimized.

If the wobble pit section 11 is located after the identification signal section 12, the tracking error signal cannot be sufficiently corrected because the tracking error signal correction starts only after the tracking error signal begins to have disturbances due to the pre-pits of the identification signal section 12. Moreover, in such cases, the beam spot 9 arrives at the main information signal section 13 before completing the tracking error signal correction, so that there may still be a tracking offset left at the beginning of the main information signal section 13.

In the optical disk of the present example, one complete round of a track is divided into a plurality of sectors. The synchronization signal section 10, the wobble pit section 11, and the identification signal section 12 as shown in FIG. 1 are provided at the beginning of each sector. In the case of a CAV control system, the sectors are disposed radially along the radius direction of the disk. It is also applicable to combine a number of tracks to form one zone, thereby dividing the disk into a plurality of such zones, and perform a CAV control for each zone.

Figure 2:
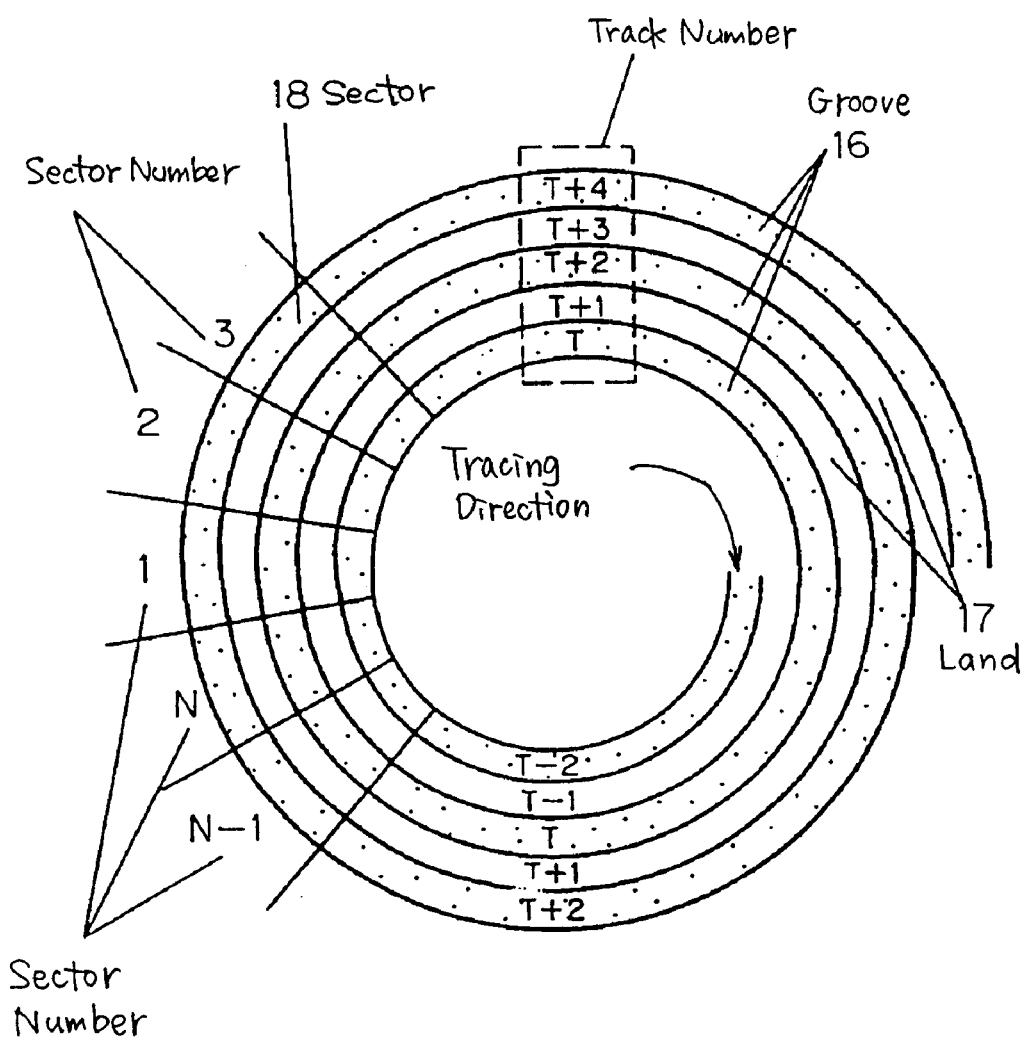
FIG. 2 is a view showing the configuration of information tracks of the optical disk shown in FIG. 1.

Next, the track format of the optical disk of the present example will be described. FIG. 2 is a view showing the configuration of information tracks of the optical disk. The optical disk in FIG. 2 includes grooves 16 and lands 17. Information track numbers (T, T+1, T+2, T+3, T+4, etc.) are sequentially assigned to the respective rounds of tracks, irrespective of whether they are lands or grooves.

A beam spot travels anticlockwise from the inner periphery to the outer periphery of the disk.

Each track is divided into a number N of sectors 18, the sectors being sequentially numbered as $1^{st}$ to $N^{th}$.

Since the information tracks form a spiral as a whole, the $N^{th}$ sector in a $T^{th}$ track lies continuously with the $1^{st}$ sector of a $T+2^{th}$ track in the grooves. Similarly, in the lands, the Nth sector in a $T+1^{th}$ track lies continuously with the $1^{st}$ sector of a $T+3^{th}$ track. These information track numbers and the sector numbers have previously been formed in the form of pre-pits as described above.

In the present example, the address data in the "groove" tracks is recorded in the form of pre-pits. In the case where a "land" track is traced in this configuration, the information of a given location is obtained simply by adding one to the track number of the address data obtained by reproducing the pre-pits. Since the same sector number is shared by adjoining sectors along the radius direction of the disk, signals obtained by reproducing the pre-pits in the "groove" and "land" information tracks can be equally used as locational information.

Figure 3:
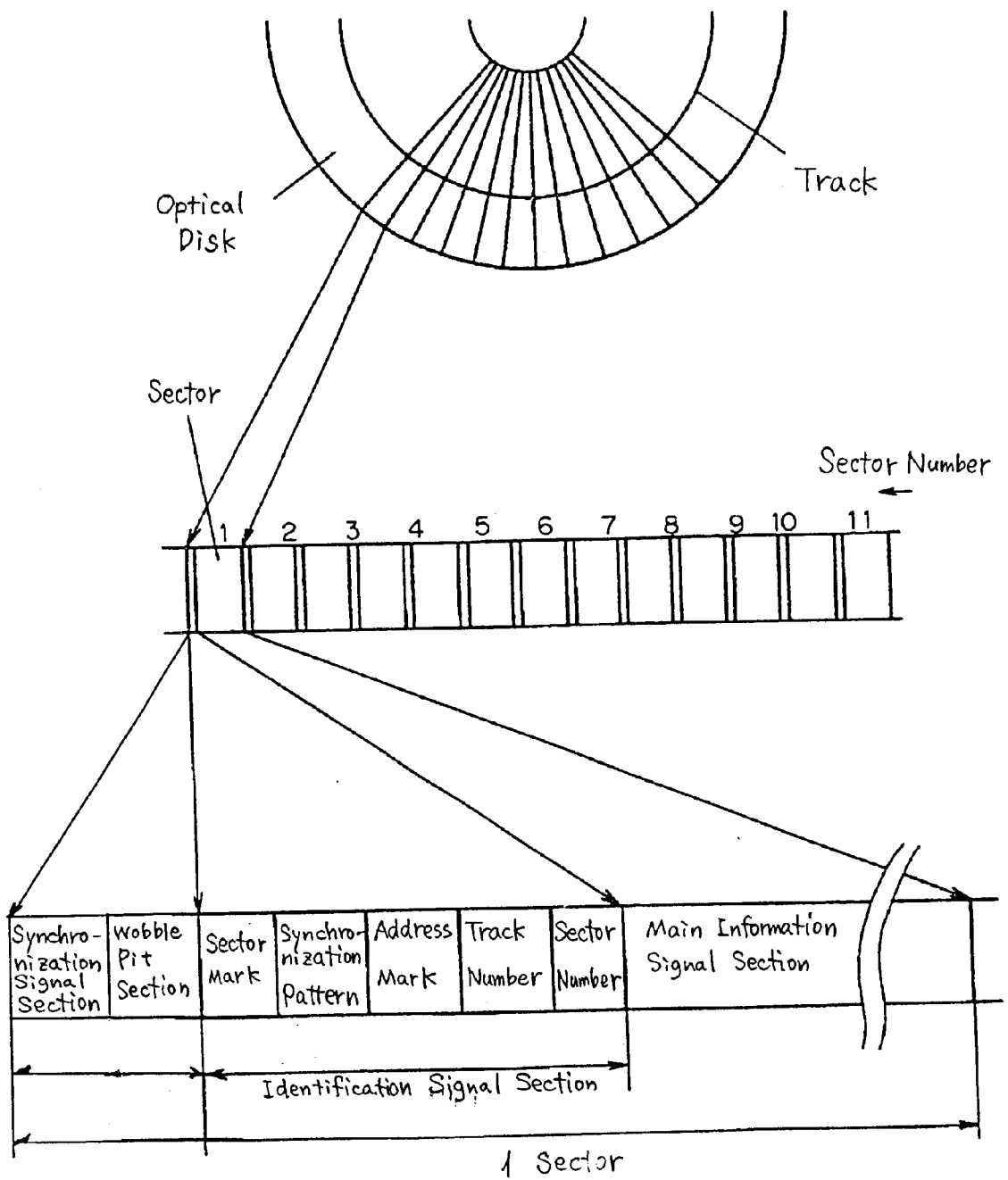
FIG. 3 is a diagram describing the sector format of the optical disk shown in FIG. 1.

FIG. 3 is a diagram describing the format of identification signals corresponding to one sector. As shown in FIG. 3, one sector consists of a synchronization signal section, a wobble pit section, an identification signal section, and a main information signal section. The identification signal section further includes blocks indicating: a sector mark, a synchronization pattern, an address mark, a track number, and a sector number, respectively. The functions of the respective blocks are as follows:

1) Sector mark: indicates a beginning of a sector
2) Synchronization pattern: generates a clock for address data reproduction.
3) Address mark: indicates a beginning of address data.
4) Track number, sector number: indicate address data.

Among the above, the sector mark, the synchronization pattern, and the address mark are fixed or identical in all sectors.

Next, an optical information recording/reproducing device capable of recording, reproducing or erasing information signals on the optical disk according to the present example will be described with reference to FIG. 4.

Figure 4:
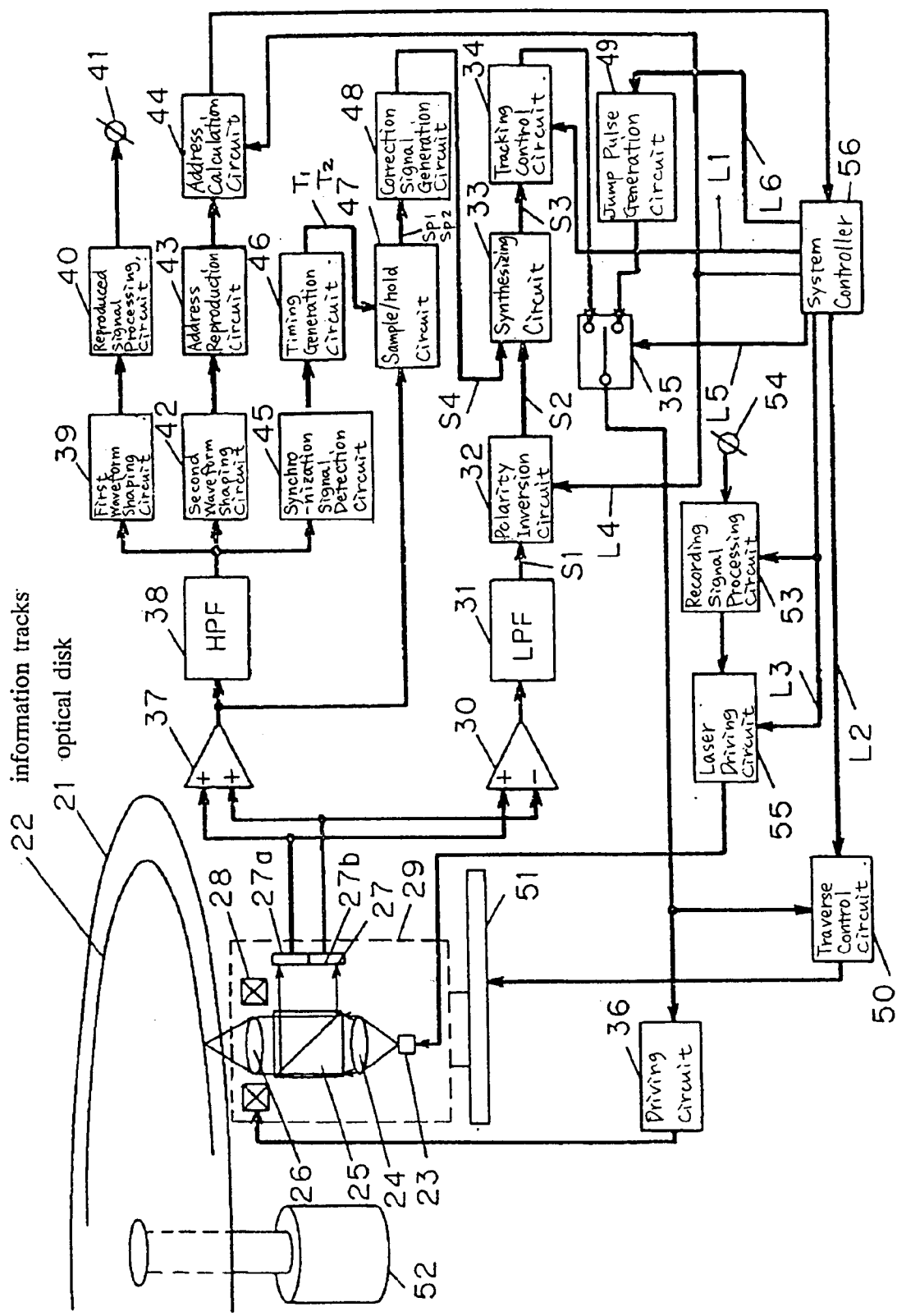
FIG. 4 is a block diagram showing the configuration of an optical information recording/reproduction device for the optical disk shown in FIG. 1.

An optical disk 21 shown in FIG. 4 has the above-described structure, including "land" and "groove" information tracks 22. Information can be recorded on or reproduced from the optical disk 21 by using the optical information recording/reproducing device in FIG. 4.

First, the structure of an optical head 29 will be described. The optical head 29 includes a semiconductor laser element 23, a collimating lens 24 for collimating laser light emitted from the semiconductor laser element 23, a half mirror 25, an objective lens 26 for converging the collimated light led through the half mirror 25 onto an information surface of the optical disk 21, an optical detector 27 for receiving light reflected from the optical disk 21 via the objective lens 26 and the half mirror 25, and an actuator 28 supporting the objective lens 26. The optical detector 27 includes two light receiving portions 27a and 27b for generating a tracking error signal, the light receiving portions 27a and 27b defining two integral portions of the optical detector 27 divided in parallel to the direction of tracks on the optical disk 21. These elements of the optical head 29 are mounted on a head base (not shown).

The outputs of the optical pickup 29 (i.e., detected signals output from the light receiving portions 27a and 27b of the optical detector 27) are input to a differential amplifier 30 and an addition amplifier 37. The output of the differential amplifier 30 is input to a low-pass filter (LPF) 31. The LPF 31 receives a differential signal from the differential amplifier 30, and outputs a signal S1 to a polarity inversion circuit 32. The polarity inversion circuit 32 receives the signal S1 from the LPF 31 and a control signal L4 from a system controller 56 (described later), and outputs a signal S2 to a synthesizing circuit 33.

On the other hand, the output of the addition amplifier 37 (an addition signal) is coupled to a high-pass filter (HPF) 38. The HPF 38 outputs high frequency components of the addition signal to a first waveform shaping circuit 39, a second waveform shaping circuit 42, and a synchronization signal detection circuit 45. The first waveform shaping circuit 39 receives the high frequency components of the addition signal from the HPF 38 and outputs a digital signal to a reproduced signal processing circuit 40 (described later). The reproduced signal processing circuit 40 outputs a reproduced information signal to an output terminal 41. The second waveform shaping circuit 42 receives the high frequency components of the addition signal from the HPF 38 and outputs a digital signal to an address reproduction circuit 43 (described later). The address reproduction circuit 43 receives the digital signal from the second waveform shaping circuit 42, and outputs first address data to an address calculation circuit 44 (described later). The address calculation circuit 44 receives the first address data from the address reproduction circuit 43 and a control signal L1 from the system controller 56, and outputs second address data to the system controller 56.

The synchronization signal detection circuit 45 receives the high frequency components of the addition signal from the HPF 38 and outputs a detected synchronization signal to a timing generation circuit 46. The timing generation circuit 46 receives the detected synchronization signal and outputs a timing pulse to a sample/hold circuit 47. The sample/hold circuit 47 receives the addition signal from the addition amplifier 37 and the timing pulse from the timing generation circuit 46, and outputs a sampling signal to a correction signal generation circuit 48. The correction signal generation circuit 48 receives the sampling signal from the sample/hold circuit 47, and outputs a correction signal S4 to the correction signal generation circuit 48.

The synthesizing circuit 33 receives the signal S2 from the polarity inversion circuit 32 and the signal S4 from the correction signal generation circuit 48, and outputs a signal S3 to a tracking control circuit 34.

The tracking control circuit 34 receives the signal S3 from the synthesizing circuit 33 and the control signal L1 from the system controller 56, and outputs a tracking control signal to one of the two input terminals of a first selector 35. The first selector 35 receives the tracking control signal from the tracking control circuit 34, a driving pulse from a jump pulse generation circuit 49, and a control signal L5 from the system controller 56, so as to output a driving signal to a driving circuit 36 and a traverse control circuit 50.

The driving circuit 36 receives the driving signal from the first selector 35, and outputs a driving current to the actuator 28.

When the main information signal reproduced from recording marks and the identification signals reproduced from pre-pits have different reproduction amplitude levels, the first waveform shaping circuit 39 and the second waveform shaping circuit 42 are adapted to have different gains.

The jump pulse generation circuit 49 receives a control signal L6 from the system controller 56 and outputs a driving pulse to the first selector 35.

The traverse control circuit 50 receives a control signal L2 from the system controller 56 and the tracking control signal from the first selector 35, and outputs a driving current to a traverse motor 51.

The traverse motor 51 moves the optical head 29 along the radius direction of the optical disk 21. A spindle motor 52 rotates the optical disk 21.

A recording signal processing circuit 53 receives information signals (e.g., audio/video signals and computer data) via an external input terminal 54 and a control signal L3 from the system controller 56, and outputs a recording signal to a laser driving circuit 55 (described later). The laser driving circuit 55 receives the control signal L3 from the system controller 56 and the recording signal from the recording signal processing circuit 53, and outputs a driving current to the semiconductor laser element 23.

The system controller 56 receives the second address data from the address calculation circuit 44. The system controller 56 outputs the control signal L1 to the tracking control circuit 34, the control signal L2 to the traverse control circuit 50, the control signal L3 to the recording signal processing circuit 53 and the laser driving circuit 55, the control signal L4 to the polarity inversion circuit 32 and the address calculation circuit 44, the control signal L5 to the first selector 35, and the control signal L6 to the jump pulse generation circuit 49.

Next, the operations of the above-described optical information recording/reproduction device will be described with reference to FIG. 4.

First, the operation of reproducing information signals will be described.

The laser driving circuit 55 is placed in a reproduction mode by the control signal L3 from the system controller 56, and supplies a driving current to the semiconductor laser 23 so that the semiconductor laser 23 is driven to emit light at a predetermined intensity. The traverse control circuit 50 outputs a driving current to the traverse motor 51 in accordance with the control signal L2 from the system controller 56 so as to move the optical head 29 to a target track.

A laser beam emitted from the semiconductor laser 23 is collimated by the collimating lens 24, led through the beam splitter (half mirror) 25, and converged on the optical disk 21 by the objective lens 26.

A light beam reflected from the optical disk 21, carrying the information in the information tracks 22 through diffraction, is led through the objective lens 26 so as to be incident on the optical detector 27 due to the beam splitter 25.

The light receiving portions 27a and 27b convert the intensity variation of the incident light beam into electric signals, and outputs the electric signals to the differential amplifier 30 and the addition amplifier 37. The differential amplifier 30 subjects the input currents to an I-V (current to voltage) conversion and thereafter takes a difference therebetween, so as to output the difference as a differential signal.

The LPF 31 extracts the low frequency components of the differential signal, and outputs the low frequency components as the signal S1 to the polarity inversion circuit 32. In accordance with the control signal L4 input from the system controller 56, the polarity inversion circuit 32 either allows the signal S1 to pass (as the signal S2) or inverts the polarities (i.e., plus or minus) thereof and outputs the result as the signal S2 to the synthesizing circuit 33.

For the sake of convenience of description, it is assumed herein that the signal S1 is allowed to pass in the case where the target track (i.e., the track carrying information to be recorded or reproduced) is a groove and that the signal S1 is inverted in the case where the target track is a land.

The synthesizing circuit 33 adds the signal S4 from the correction signal generation circuit 48 to the signal S2 so as to output the result as the signal S3 to the tracking control circuit 34. Herein, the signal S2 is a so-called "push-pull tracking error signal" which corresponds to the tracking error amount between the beam spot converged on the information surface of the optical disk 21 and the center of the target information track. The signal S4 (which will be described later) corresponds to the offset amount of the push-pull signal. The synthesizing circuit 33 cancels the redundant offset components in the signal S2 by adding the signal S4 thereto.

The tracking control circuit 34 outputs a tracking control signal to the driving circuit 36 via the first selector 35 in accordance with the level of the input signal S3. The driving circuit 36 supplies a driving current to the actuator 28 in accordance with the tracking control signal, whereby the position of the objective lens 26 is controlled along the direction across the information track 22. As a result, the beam spot properly scans the center of the information track 22.

The traverse control circuit 50 receives the tracking control signal, and drives the traverse motor 51 in accordance with the low frequency components of the tracking control signal so as to gradually move the optical head 29 along the radius direction of the optical disk 21 as the reproduction operation proceeds.

The first selector 35 connects/disconnects the output of the jump pulse generation circuit 49 to/from the input of the driving circuit 36 in accordance with the control signal L5 from the system controller 56. The control signal L5 controls the first selector 35 so as to couple the output of the jump pulse generation circuit 49 to the input of the driving circuit 36 only when moving the beam spot between information tracks, that is, when a "track jump" is made. Otherwise, the first selector 35 couples the input of the driving circuit 36 to the tracking control circuit 34.

On the other hand, a focus control circuit (not shown) controls the position of the objective lens 26 along a direction perpendicular to the disk surface so that the beam spot accurately focuses on the optical disk 21.

Once the beam spot is accurately positioned on the information track 22, the addition amplifier 37 subjects the output currents from the light receiving portions 27a and 27b to an I-V conversion, and thereafter adds the converted currents to output the result as an addition signal to the HPF 38.

The HPF 38 cuts off the unnecessary low frequency components of the addition signal, and allows the reproduced signals (i.e., the main information signal and the address signal) as signals having analog waveforms, which are output to the first waveform shaping circuit 39, the second waveform shaping circuit 42, and the synchronization signal detection circuit 45.

The second waveform shaping circuit 42 subjects the address signal having an analog waveform to a data slice process using a second threshold value, thereby converting the address signal into a signal having a pulse waveform, which is output to the address reproduction circuit 43.

The address reproduction circuit 43 demodulates the input digital address signal, and outputs the demodulated digital address signal as the first address data to the address calculation circuit 44.

The address calculation circuit 44 determines whether the track currently scanned by the beam spot is a land or a groove based on the control signal L4. If the currently scanned track is a land, the address calculation circuit 44 adds one to the track number contained in the first address data and outputs the result, along with the sector number, as the second address data to the system controller 56.

Based on the second address signal, the system controller 56 determines whether or not the beam spot is on a target address. If the beam spot is on the target address, the control signals L4 and L5 are maintained so that the beam spot proceeds to trace the main information signal section. While the beam spot traces the main information signal section, the first waveform shaping circuit 39 subjects the main information signal having an analog waveform (which is received via the optical detector 27, the addition amplifier 37, and the HPF 38) to a data slice process using a first threshold value, thereby converting the main information signal into a digital signal, which is output to the reproduced signal processing circuit 40.

The reproduced signal processing circuit 40 demodulates the input digital main information signal, and subjects the demodulated digital main information signal to appropriate processes (e.g., error correction) before it is output at the output terminal 41.

When the beam spot travels over the synchronization signal section, the synchronization signal detection circuit 45 detects a synchronization signal from reproduced signals (received via the optical detector 27, the addition amplifier 37, and the HPF 38), and outputs the detected synchronization signal to the timing generation circuit 46. Upon receiving the detected synchronization signal, the timing generation circuit 46 outputs two timing pulses T1 and T2, at a predetermined time interval, to the sample/hold circuit 47.

The timing pulses T1 and T2 are adapted so that the timing pulse T1 is output when the beam spot is directly above the first wobble pits 14 and that the timing pulse T2 is output when the beam spot is directly above the second wobble pits 15, in view of the distance between the first wobble pits 14 and the synchronization signal and the distance between the second wobble pits 15 and the synchronization signal on the disk 21, and the travelling speed of the beam spot.

The gap G1 in FIG. 1 is prescribed to be a distance which is travelled by the beam spot 9 after the beam spot 9 passes over the synchronization signal section 10 and before a synchronization signal is detected and timing pulses are output by the timing generation circuit 46.

When the timing pulse T1 or T2 is input to the sample/hold circuit 47, the sample/hold circuit 47 sample and holds the voltage value of the addition signal input from the addition amplifier 37 at that moment, and correspondingly outputs a sampling signal SP1 or SP2 to the correction signal generation circuit 48.

The correction signal generation circuit 48 takes a difference between the sampling signals SP1 and SP2, and amplifies or attenuates the difference by a predetermined gain AG1 so as to output the result to the synthesizing circuit 33 as the correction signal S4. The synthesizing circuit 33 cancels the residual offset components in the push-pull signal S2 input from the polarity inversion circuit 32 by adding the correction signal S4 thereto, so as to output the signal S3 to the tracking control circuit 34. The signal S3 is a tracking error signal having an improved accuracy as compared to that of the signal S2.

The residual offset components in the push-pull signal S2, which are cancelled in the above operation, typically emerge due to a tilt of the optical disk 21 along the radius direction, for example. If such an offset component is present in the DC offset of the signal S2, it is impossible to completely eliminate the tracking error between the beam spot 9 and the center line of the target information track by tracking control using only the signal S2. According to the present invention, until beam spot 9 has travelled past the identification signal section 12, the signal S3 is maintained at the value taken immediately before the beam spot 9 started travelling over the identification signal section 12. As a result, the tracking error signal is prevented from having a large variation at the identification signal section due to an offset of the beam spot 9 from the pre-pits. Therefore, the beam spot 9 stably and accurately traces the center line 19 of the information track. Moreover, the residual offset correction using the correction signal S4 is performed before the beam spot 9 arrives at the identification signal section, so that the identification signals can be stably read out.

The gap G2 in FIG. 1 is prescribed to be equal to a distance which is travelled by the beam spot 9 after the beam spot 9 has gone past the second wobble pits 15 and before the synthesizing circuit 33 outputs the correction signal S4. Thus, the beam spot 9 does not start tracing the identification signal section 12 until the residual offset in the tracking control has been removed. As a result, the beginning portion of the identification signal section 12 is prevented from being misdetected due to an off-tracking.

During recording, the system controller 56 informs the recording signal processing circuit 53 and the laser driving circuit 55 with the control signal L3 that the operation is in a recording mode.

The recording signal processing circuit 53 adds an error correction code, etc., to an audio signal and the like which are input via the external input terminal 54, and outputs the signal as an encoded recording signal to the laser driving circuit 55. Once the laser driving circuit 55 is placed in a recording mode by the control signal L3, the laser driving circuit 55 modulates a driving current applied to the semiconductor laser 23 in accordance with the recording signal. As a result, the intensity of the beam spot 9 radiated onto the optical disk 21 changes in accordance with the recording signal, whereby recording pits are formed.

During reproduction, on the other hand, the control signal L3 places the laser driving circuit 55 in a reproduction mode, and the laser driving circuit 55 controls the driving current so that the semiconductor laser 23 emits light with a constant intensity which is lower than the light intensity during the recording mode.

While the above operations are performed, the spindle motor 52 rotates the optical disk 21 at a constant angular velocity.

Next, an operation of moving the beam spot 9 to a target address (hereinafter referred to as a "seek operation") will be described in more detail.

Once an address is designated from which to start recording/reproduction, the system controller 56 determines whether the sector of the designated address is included in a land track or a groove track (by referring to an address map or the like), and outputs the judgment result as the control signal L4.

Herein, it is assumed that the control signal L4 is at a Lo (Low) level when the sector having the designated address is in a groove, and a Hi (High) level when the sector of the designated address is in a land. The polarity inversion circuit 32 inverts the polarities of the input signal if the start address is an address within a land. The polarity inversion circuit 32 does not invert the polarities of the input signal if the start address is an address within a groove. The system controller 56 supplies the control signal L5 to the first selector 35 so that the tracking control circuit 34 is selected as the input source of the driving circuit 36. At this time, the tracking control circuit 34 is controlled by the control signal L1 not to output a tracking control signal.

Next, the control signal L2 is sent to the traverse control circuit 50 so as to drive the traverse motor 51 for a "coarse" seek movement. This "coarse" seek movement is made by previously calculating the number of tracks present between the current address (i.e., the address before the movement) and the target address, based on the values of the current and target addresses, and comparing the pre-calculated number with the number of tracks traversed during the movement (which is derived from the tracking error signal).

Then, the control signal L1 causes the tracking control circuit 34 to output a tracking control signal to the driving circuit 36 and the traverse control circuit 50, so that the beam spot 9 roughly traces a land or a groove. Once a tracking lock-in procedure is complete, address data from the identification signal section is reproduced. That is, the first address data is input to the address calculation circuit 44 via the optical detector 27, the addition amplifier 37, the HPF 38, the second waveform shaping circuit 42, and the address reproduction circuit 43.

The address calculation circuit 44 regards the first address data as the current address while the control signal L4 is at the Lo level, and outputs the first address data as the second address data to the system controller 56. On the other hand, while the control signal L4 is at the Hi level, the address calculation circuit 44 adds one to the track number in the address data, and outputs the result as the second address data to the system controller 56.

The system controller 56 compares the second address data against the target address value. If there is a difference of 1 track or more between the track number in the second address data and that of the target address value, the system controller 56 causes the first selector 35 to couple the output of the jump pulse generation circuit 49 with the input of the driving circuit 36 based on the control signal L5. In addition, the system controller 56 causes the traverse control circuit 50 not to output a driving signal to the traverse motor 51 by using the control signal L2. Subsequently, the system controller 56 causes the jump pulse generation circuit 49 to output a driving pulse to driving circuit 36 based on the control signal L6, the driving pulse corresponding to the above-mentioned difference in track numbers.

The driving circuit 36 supplies a driving current corresponding to the driving pulse to the actuator 28, and causes the beam spot 9 to make a "track jump" by a designated number of tracks. Once the track jump by the designated number of tracks is complete, then a tracking lock-in procedure is performed, and after the beam spot 9 has arrived at the target sector due to the rotation of the optical disk 21, the recording/reproduction of information signals is started in this sector.

Figure 5:
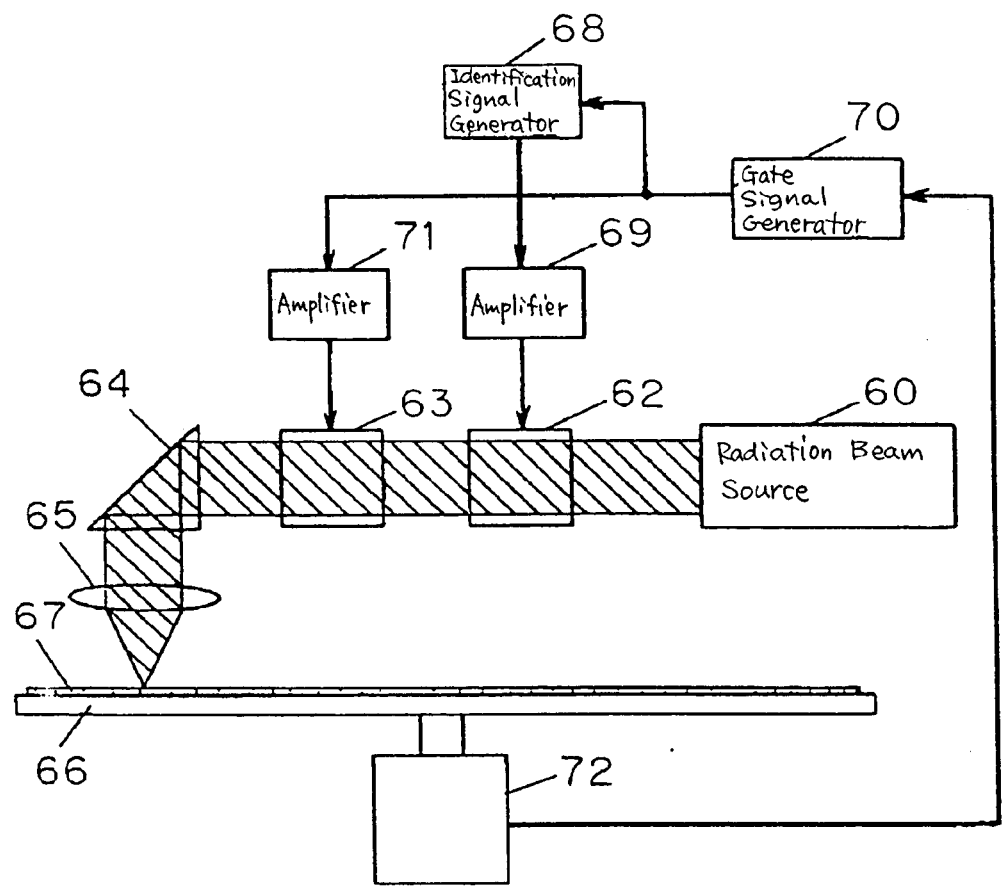
FIG. 5 is a block diagram illustrating an essential portion of a device for producing the optical disk shown in FIG. 1.

The optical disk 21 according to the present example can be produced by applying the method described in Japanese Laid-Open Patent Publication No. 50-68413, for example. A device for producing the optical disk 21 of the present example will now be briefly described with reference to FIG. 5. FIG. 5 is a block diagram illustrating the device.

In the device shown in FIG. 5, a radiation beam source 60 (e.g., a laser light source) emits a radiation beam with sufficient energy. The radiation beam travels through a light intensity modulator 62, an optical deflector 63, and a mirror prism 64 so as to be converged onto a minute radiation beam spot by the objective lens 65. A radiation beam sensing layer 67 (e.g., a photoresist layer) is applied on a recording medium 66 (e.g., an optical disk substrate).

The light intensity modulator 62 occasionally interrupts the radiation beam in accordance with identification signals input from an identification signal generator 68 via an amplifier 69. As a result, the identification signals output from the identification signal generator 68 are converted into radiation beam pulses, which in turn are converted into a pit array on the radiation beam sensing layer 67 through reaction to light. The identification signal generator 68 generates an identification signal when a gate pulse from a gate signal generator 70 is input thereto. The light intensity modulator 62 can be composed of, for example, a photoelectric crystal which rotates the deflection direction of a radiation beam responsive to a voltage applied thereto and an optical analyzer for converting changes of the direction of the deflection plane into changes in light intensity.

The optical deflector 63 varies the angle of the radiation beam by a very small angle, only while a gate pulse from the gate signal generator 70 is input to the optical deflector 63 via an amplifier 71, so that the minute radiation beam spot is moved on the recording medium 66 by a predetermined width along the radius direction.

The gate signal generator 70 outputs a gate pulse (having a length equal to that of an identification signal section) to the identification signal generator 68 and the amplifier 71 at a predetermined period in synchronization with a rotation phase signal output from a motor 72 for rotating the recording medium 66. Thus, a continuous track is written on the radiation beam sensing layer 67 with no gate pulses being generated. On the other hand, when a gate pulse is generated, an identification signal is written in the form of a pit array at a position away from the continuous track by a predetermined length along the radius direction.

Thus, a continuous track and a pre-pit array of identification signals can be written on the radiation beam sensing layer 67 in one sequence of steps. In other words, the identification signals are presented in the form of disruptions between continuous tracks. If it is desirable to form a large pre-pit 8 (such as the pre-pits in the synchronization signal section 10), the intensity of the radiation beam can be increased by corresponding amount. After the writing process is complete, steps including etching, transcription, and molding are performed, whereby a disk substrate is accomplished.

EXAMPLE 2

Figure 6:
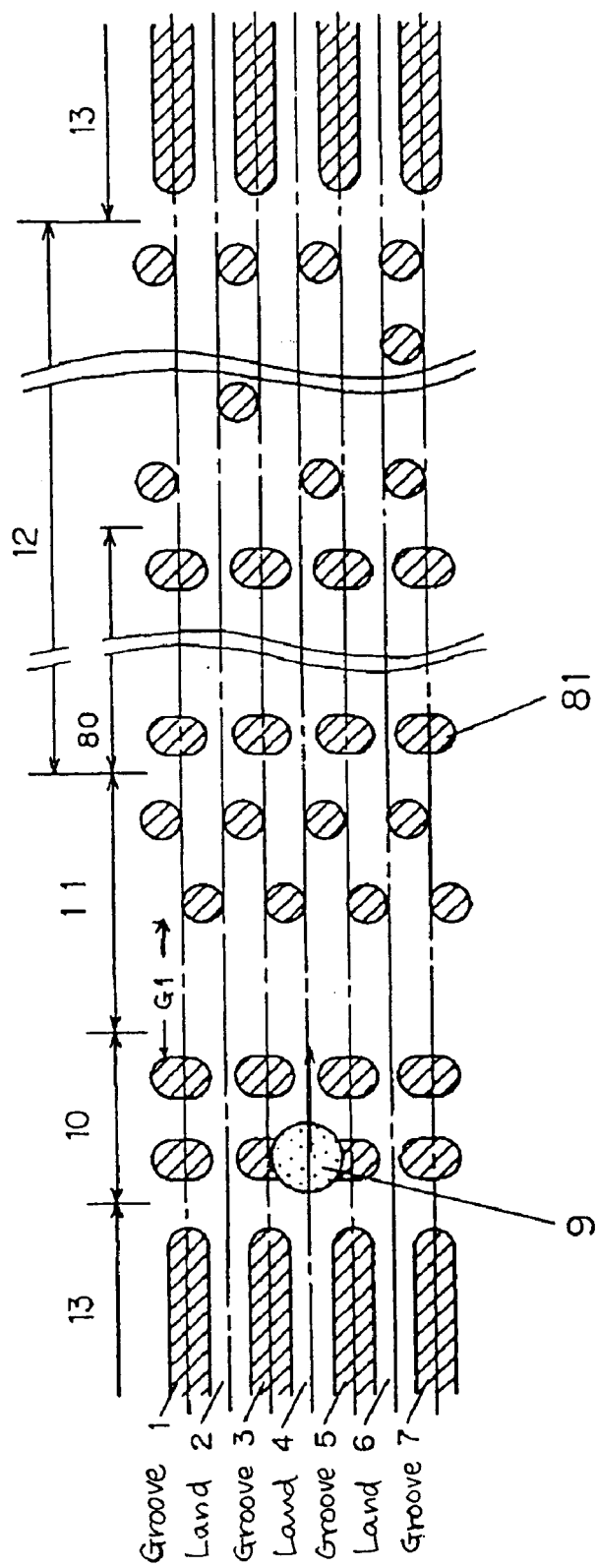
FIG. 6 is a magnified plan view showing an essential portion of the optical disk according to another example of the present invention.

Although the optical disk of Example 1 illustrated in FIG. 1 includes the gaps G1 and G2 provided before and after the wobble pit section 11, it is also applicable to form, as shown in FIG. 6, a wobble pit section 11 adjoining a sector mark block 81 of wide pits, thereby omitting the gap G2.

The sector marks are fixed patterns, and therefore identical regardless of the track, e.g., between adjoining tracks. Therefore, even if the beam spot 9 goes off the track center, the beam spot 9 will still be partially on the adjoining sector mark, thereby reducing the liability of misdetecting sector marks. Moreover, the synthesizing circuit 33 outputs the signal S3 before the beam spot 9 has travelled past the sector mark block, so that the residual offset in the tracking control is eliminated. By adopting wide pits 81 for the sector mark pre-pits as shown in FIG. 6, the detection accuracy of sector marks can be further enhanced.

Among the various blocks in the identification signal section illustrated in FIG. 3, the synchronization pattern, the address mark, and the sector number are also identical regardless of the track. Therefore, the detection of these pre-pits can also be further enhanced by adopting wide pits for such pre-pits.

EXAMPLE 3

Figure 7:
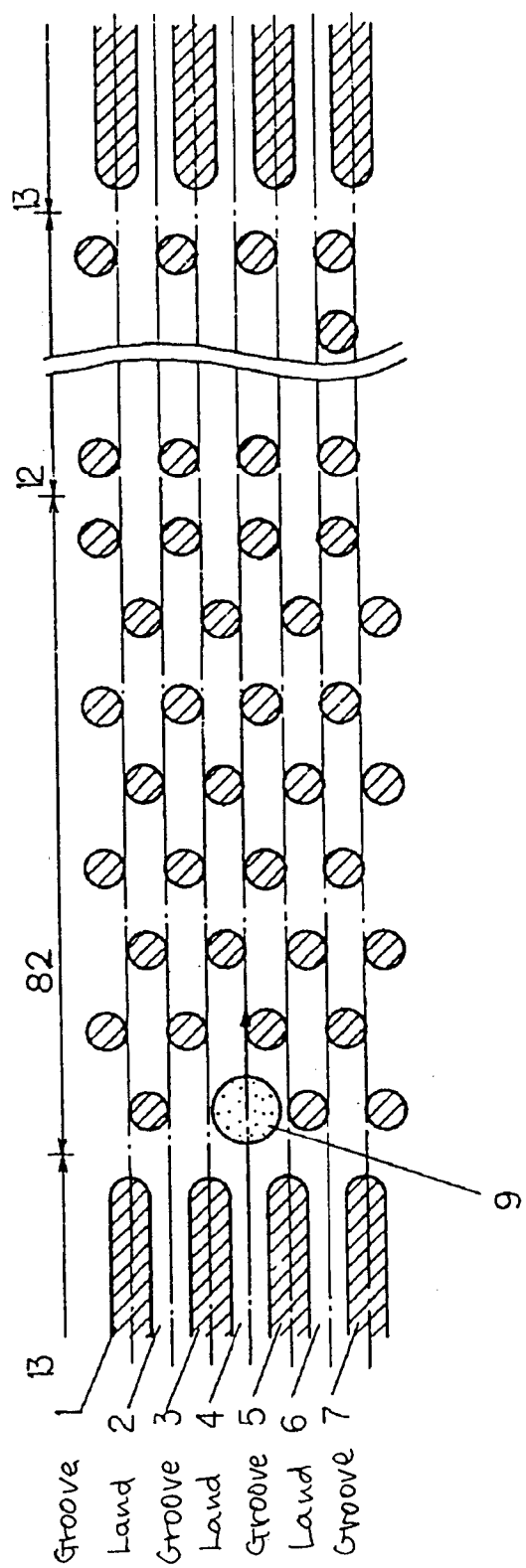
FIG. 7 is a magnified plan view showing an essential portion of the optical disk according to still another example of the present invention.

It is also applicable to provide wobble pits immediately after the main information signal section consisting of lands and grooves. FIG. 7 illustrates an example of such configuration. Reference numeral 82 denotes a wobble pit section including a number of pairs (four pairs in FIG. 7) consisting of first wobble pits and second wobble pits. The first pair serves the function of the synchronization signal section 10 in FIG. 1. The first and second wobble pits are both disposed between the center lines of adjoining information tracks so that a half of the beam spot traces on the wobble pits. Therefore, these wobble pits can be detected in the same manner as the pre-pits of the identification signal section 12.

By adopting wobble pits for the synchronization pre-pits, it becomes unnecessary to employ wide pits such as those shown in FIG. 1, thereby facilitating the production of the disk.

It is also applicable to employ a plurality of wobble pits so as to enable plural times of detection of the residual offset in tracking control. In this case, the accuracy of residual offset detection improves so that the beam spot can trace the track center even more accurately, thereby improving the tracking control stability and the detection accuracy of identification signals.

Although the pre-pits of the identification signal section 12 are provided between the center lines of lands and grooves in the optical disk of the present example, the pre-pits of the identification signal section 12 do not have to be provided exactly in the middle between the center lines of lands and grooves, but may be slightly shifted toward the groove or the land. In such cases, the amplitude of the reproduced waveforms of the identification signals may vary depending on whether they correspond to a land or a groove, but an appropriate waveform shaping can be achieved in either case, by switching between two levels of threshold values (i.e., one for the lands and the other for the grooves) in the data slicing performed in the second waveform shaping circuit.

For example, in the case where the disk substrate has been produced in such a manner that the pre-pits are shifted toward a land from the exact middle between the land and the groove, the amplitudes of the reproduced identification signals become larger in the lands than in the grooves. Therefore, it is desirable to accordingly increase the threshold value for the lands.

Such an optical disk results in a smaller disturbance in the push-pull tracking error signal than in the case where the pre-pits in the identification signal section 12 are disposed in the exact middle between a land and a groove, and therefore contributes to a more stable tracking control.

EXAMPLE 4

Although the detection of the residual offset in tracking control was based on the wobble pits provided on the optical disk in Example 3, the same effect can also be attained by meandering (wobbling) the grooves toward right and left. Specifically, the offset amount between the beam spot and a given information track can be detected by utilizing the modulation component of the returned light due to the meandering of the information track as scanned by the beam spot. Hereinafter, the principle thereof will be described with reference to FIG. 8.

Figure 8:
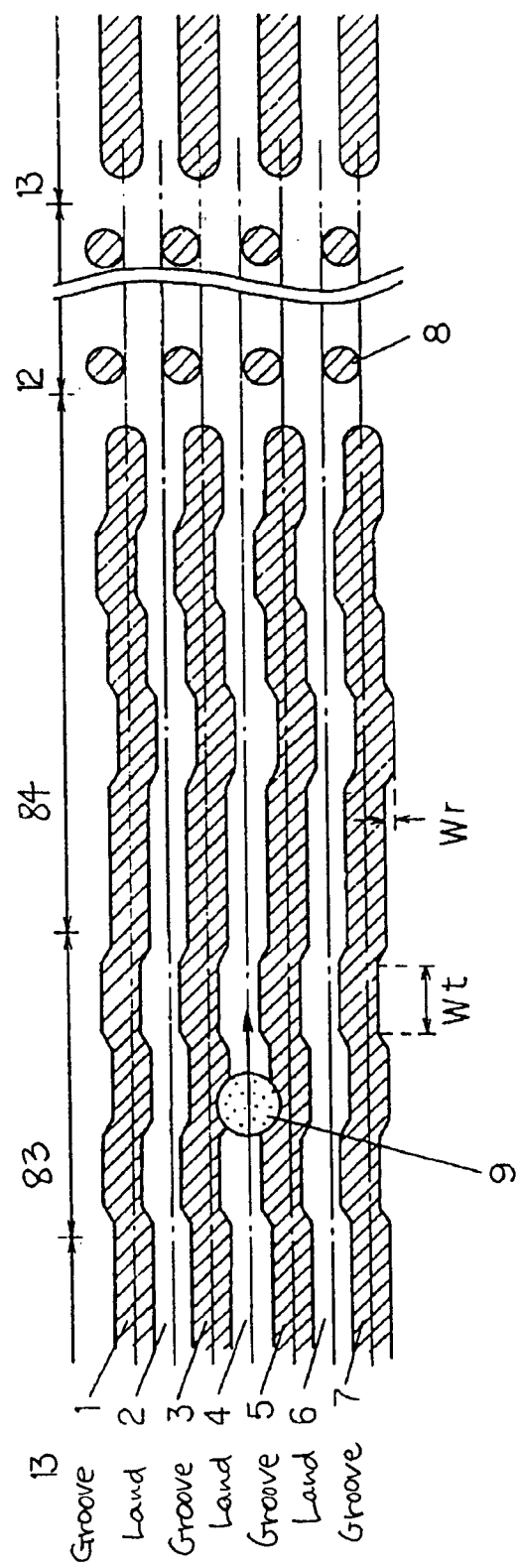
FIG. 8 is a magnified plan view showing an essential portion of the optical disk according to still another example of the present invention.
Figure 9:
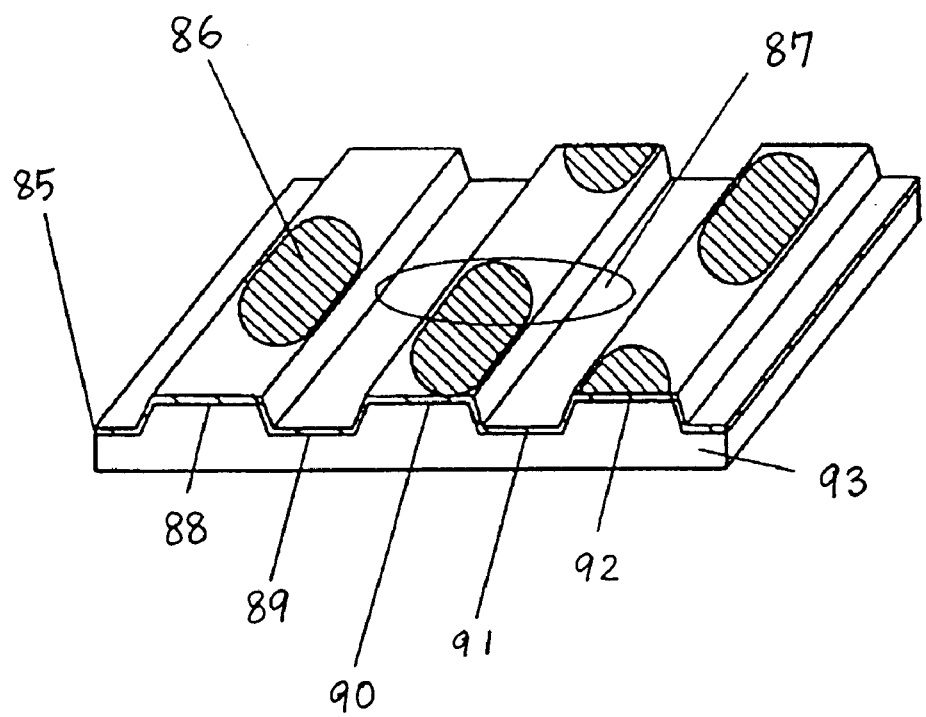
FIG. 9 is a magnified perspective view showing a conventional optical disk.
Figure 10:
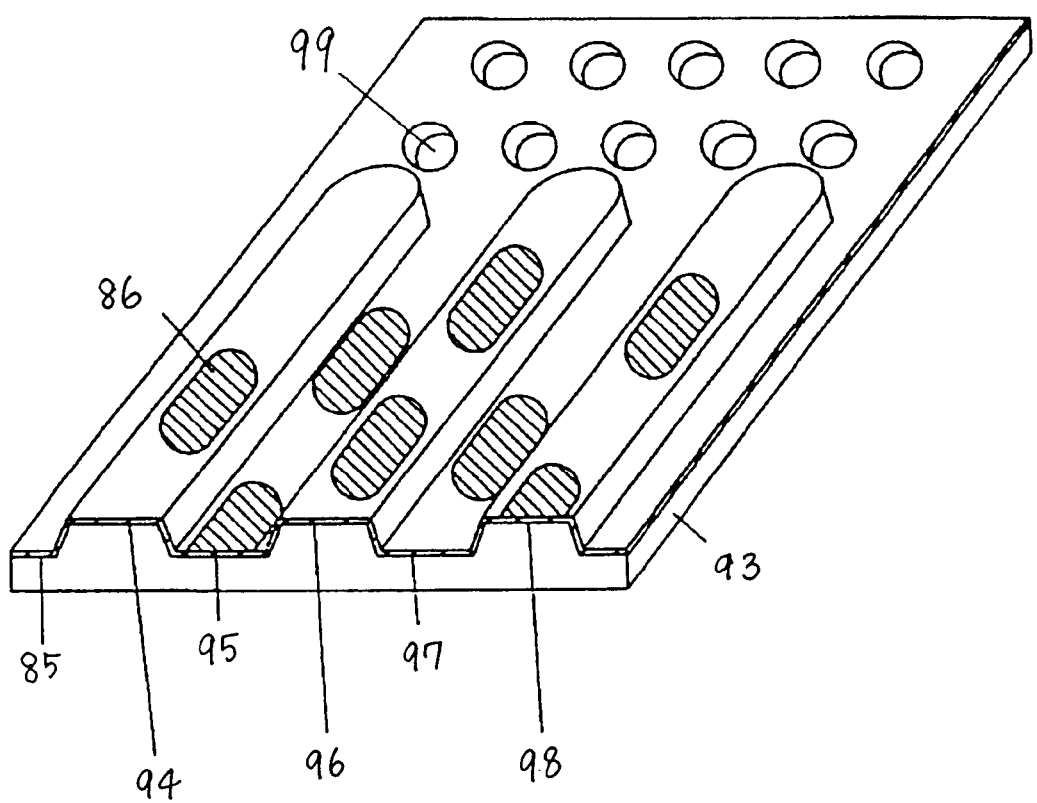
FIG. 10 is a magnified perspective view showing an optical disk in which information is recorded in both lands and grooves.

FIG. 8 is a magnified plan view showing an essential portion of an optical disk having meandering grooves. In FIG. 8, a region 83 is defined as a synchronization signal section, and a region 84 is defined as a wobble groove section. The grooves in both regions 83 and 84 are meandering.

The grooves in the synchronization signal section 83 meander with a period corresponding to the pre-pits in the synchronization signal section 10 shown in FIG. 1. The grooves in the wobble groove section 84 meander with a period equal to that period of the wobbling pre-pits in the wobble pit section 11 shown in FIG. 1.

The amount of reflected light becomes maximum when the center of the beam spot 9 is at the center of a target groove or land. Therefore, the residual offset in tracking control can be detected by sampling and comparing the amount of light reflected from the meandering grooves, as in the case of wobble pits. Moreover, meandering grooves also provide an advantage in that the grooves are not disrupted during the residual offset detection, thereby preventing the reflected light amount from having a large variation. As a result, an even more stable tracking control can be attained.

The synchronization signal can be detected by merely monitoring a push-pull signal because the grooves meander in only one direction in the synchronization section. On the other hand, the grooves in the wobble groove section can have a plurality of meanders. The accuracy of residual offset detection can be improved by conducting a plurality of samplings.

Wt in FIG. 8 defines a length over which the grooves meander away from the track centers. The value of Wt is preferably longer than the diameter of the beam spot and shorter than the minimum length followable by the tracking control for the following reasons: If the length Wt is shorter than the diameter of the beam spot, the reflected light amount is not sufficiently modulated. If the length Wt is longer than the minimum length followable by the tracking control, the beam spot will also meander along the groove or land so that the reflected light amount is not sufficiently modulated.

In general, the amplitude Wr of the meanders of the grooves shown in FIG. 8 should be ¼ or less of the groove pitch, and preferably ¼.

The timing detection for sampling residual offsets can be made by detecting the meanders of the grooves in the wobble groove section 84 and synchronously detecting the output of the addition amplifier 37 (FIG. 4), instead of detecting the synchronization signal in the synchronization signal section 83. Thus, the synchronization signal section 83 becomes unnecessary so that the area of the main information signal section 13 (FIG. 1), and hence the capacity of the optical disk, can be increased.

As for the optical disk substrate, a substrate made of glass, polycarbonate, acryl, or the like can be used. An acryl substrate is preferable for the following reason: As the present inventors described in Japanese Laid-Open Patent Publication No. 6-338064, there is a major problem of diffusion of heat to adjoining tracks during the recording of information in both lands and grooves of a rewritable recording medium. Such heat diffusion can be minimized by adopting a steep groove edge so that the recording layer is disrupted or extremely thin at the edge portion. Such grooves with steep edges are relatively easy to produce from acryl, due to its good transcribability.

Although the depth of the pre-pits was described to be equal to the depth of the grooves in Examples 1 to 4, it is also applicable to adopt a different depth for the pre-pits. By prescribing the pre-pit depth to be $\lambda/4$, in particular, the beam spot can acquire a large diffraction effect so that the degree of modulation of identification signals and the like can be increased.

EXAMPLE 5

Figure 11:
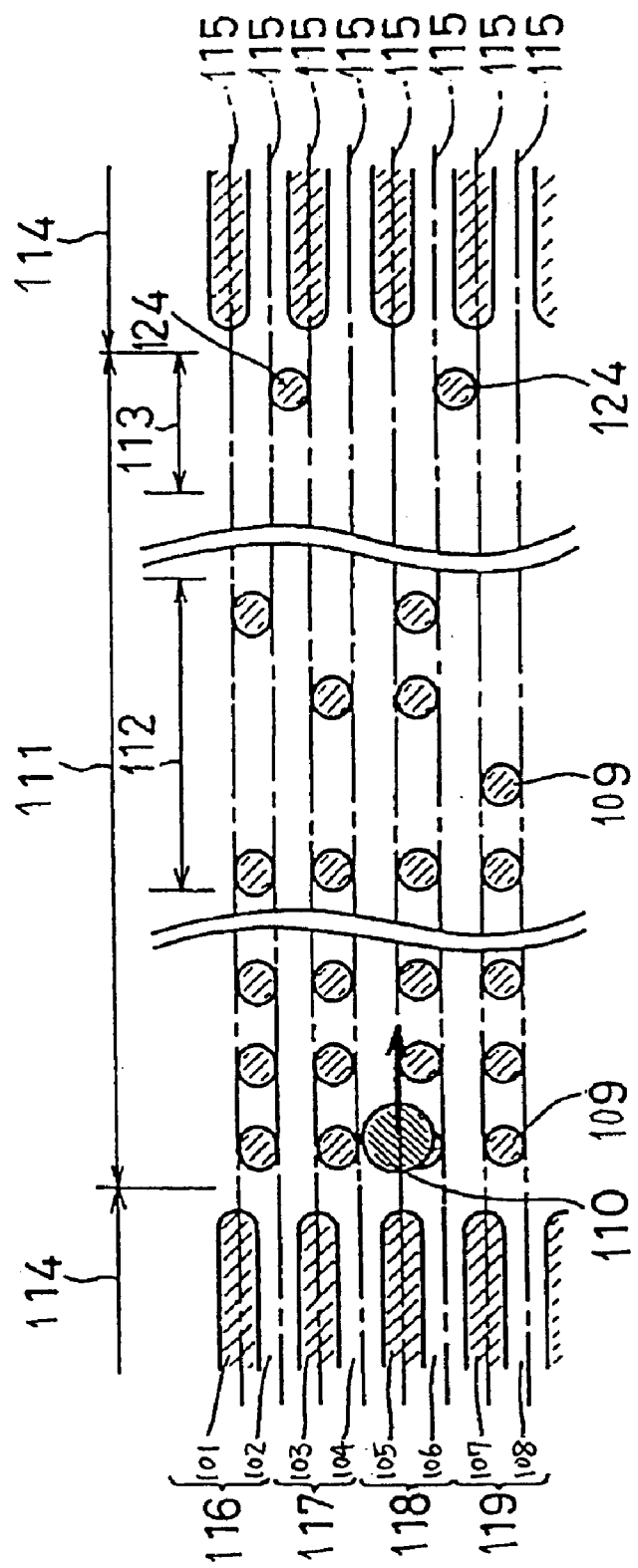
FIG. 11 is a magnified plan view showing an essential portion of the optical disk according to Example 5 of the present invention.

FIG. 11 is a magnified plan view showing an essential portion of an optical information recording medium according to Example 5 of the invention. As shown in FIG. 11, grooves 101, 103, 105, 107, . . . etc., and lands 102, 104, 106, 108, . . . etc., are alternately formed in a spiral shape on a disk substrate, thereby constituting information tracks. Herein, the grooves 101, 103, 105, 107, . . . etc., and the lands 102, 104, 106, 108, . . . etc., are formed so as to have substantially the same width. The depth of each groove can be prescribed at any value between about $\lambda/10$ and about $\lambda/4$ in terms of optical length (where $\lambda$ represents the wavelength of the laser light used for reading out information on the optical disk). In particular, the groove depth is preferably between about $\lambda/7$ and about $\lambda/5$ in order to reduce crosstalk occurring between adjoining tracks, as described in Japanese Laid-Open Patent Publication No. 5-282705.

A region 111 is defined as an identification signal section. No groove is formed in the region 111. If at all, pre-pits 109 representing identification signals are formed for every other track so as to be located between the center line 115 of a groove and the center line 115 of a land (the presence of such a pre-pit would indicate, for example, logical "1", whereas the absence of such a pre-pit would indicate, for example, logical "0"). The pre-pits 109 are formed to have a depth equal to the difference in height between the grooves and the lands. Since "tracks" refer to both grooves and lands (i.e., not only grooves), the track pitch is half of the groove pitch.

Since the pre-pits 109 indicating identification signals are formed for every other track so as to be located between the center line 115 of a groove and the center line 115 of a land, when a beam spot 110 passes over the identification signal section 111, a portion of the beam spot 110 travels over the pre-pits 109 for both lands and grooves. Therefore, the amount of reflected light is modulated by the pre-pits 109. Thus, the identification signals can be reproduced for both lands and grooves.

A region 112 is defined as a field number section constituting a portion of the identification signal section 111. Herein, a "field" refers to a pair consisting of a land and a groove adjoining each other. One field receives one field number, the field number sequentially increasing from the inner periphery or the outer periphery of the optical disk. In FIG. 11, the groove 101 and 102 are combined as a field 116; the groove 103 and 104 are combined as a field 117; the groove 105 and 106 are combined as a field 118; and the groove 107 and 108 are combined as a field 119. Thus, the pre-pits 109 in the field number section 112 are formed on the border lines between the lands and grooves belonging to the same fields.

A region 113 is defined as a track identification section constituting a portion of the identification signal section 111. In the track identification section 113, at least one track identification pre-pit 124 is formed for every other field so as to be located between the extensions of the pre-pit arrays in the field number section 112. In other words, the track identification pre-pits 124 in the track identification section 113 are located on border lines between two adjoining fields. By thus providing the track identification pre-pits 124 in the track identification section 113, it becomes possible to determine whether the beam spot 110 is tracing a land or a groove based on the reflected light of the beam spot 110 based on the principle described in more detail later.

A region 114 is defined as a main information signal section. As in conventional optical disks, recording pits in an amorphous state are formed in the main information signal section 114 in accordance with information signals of video, audio or computer data, etc.

Figure 12:
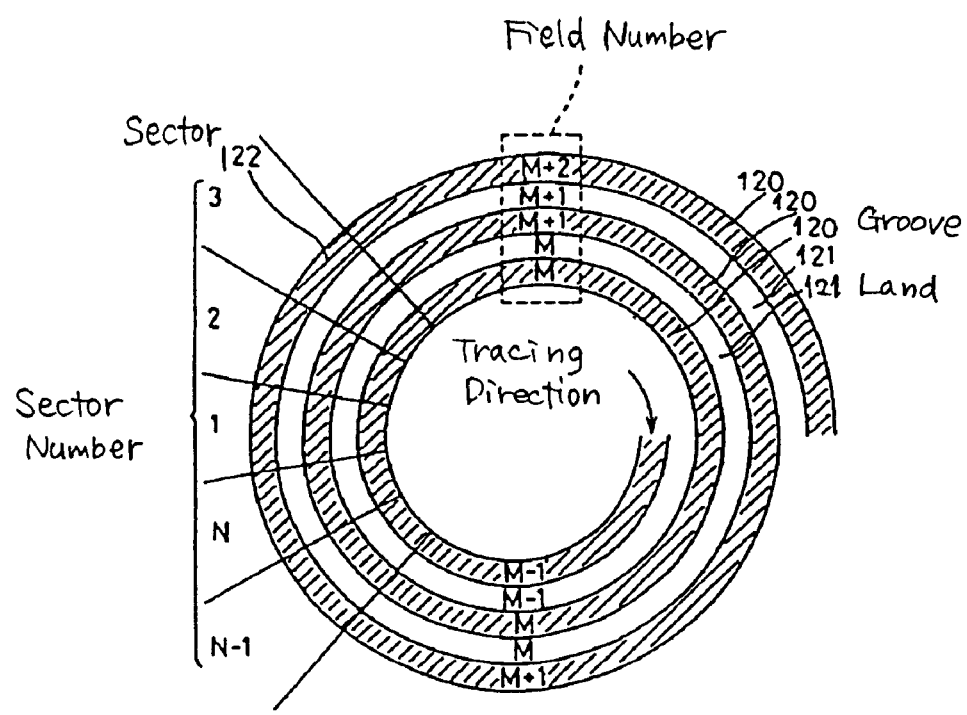
FIG. 12 is a view showing the configuration of information tracks of the optical disk shown in FIG. 11.

Next, the track format of the optical disk of the present example will be described. FIG. 12 is a view showing the configuration of information tracks of the optical disk. The optical disk in FIG. 12 includes grooves 120 and lands 121 alternately formed in a spiral shape. Field numbers (M−1, M, M+1, M+2, etc.) are sequentially assigned to the respective fields, the field numbers increasing one by one from the inner periphery toward the outer periphery.

A beam spot travels anticlockwise from the inner periphery to the outer periphery of the disk, for example.

Each track is divided into a number N of sectors 122, the sectors being sequentially numbered as $1^{st}$ to $N^{th}$.

Since the grooves 120 and the land 121 are formed in a spiral shape, the $N^{th}$ sector in an $M^{th}$ field lies continuously with the $1^{st}$ sector of an $M+1^{th}$ field.

The above-mentioned field numbers and the sector numbers are formed in the form of pre-pits 109 and 124 in the identification signal section 111 in FIG. 11. In the case of a CAV control system, the sectors are disposed radially along the radius direction of the disk. It is also applicable to combine a number of tracks to form one zone, thereby dividing the disk into a plurality of such zones, and perform a CAV control for each zone.

Figure 13:
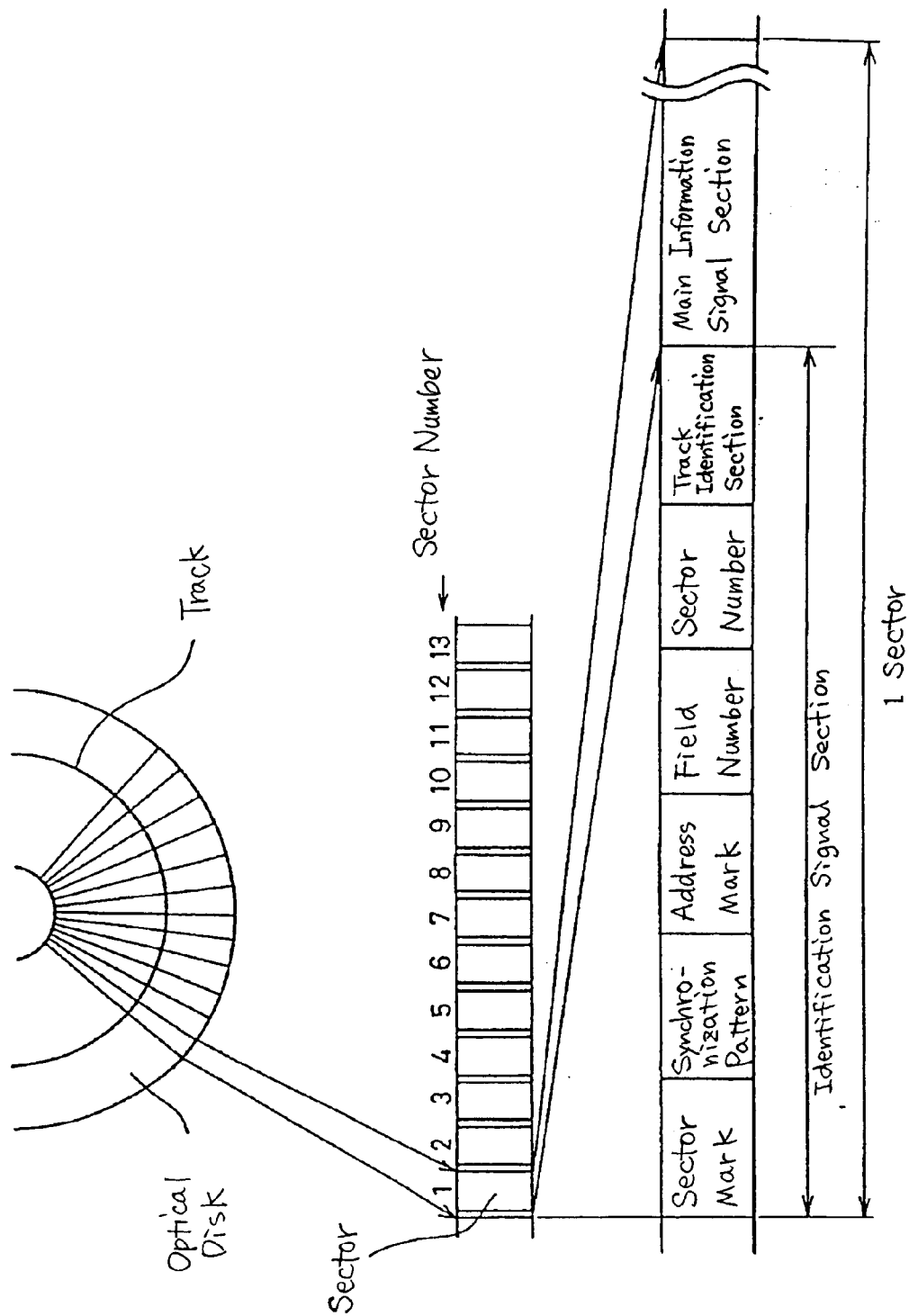
FIG. 13 is a diagram describing the sector format of the optical disk shown in FIG. 11.

FIG. 13 is a diagram describing the format of identification signals corresponding to one sector. As shown in FIG. 13, one sector consists of an identification signal section and a main information signal section. The identification signal section further includes blocks indicating: a sector mark, a synchronization pattern, an address mark, a field number, a sector number, and a track identification section, respectively. The functions of the respective blocks are as follows:

1) Sector mark: indicates a beginning of a sector
2) Synchronization pattern: generates a clock for address data reproduction.
3) Address mark: indicates a beginning of address data.
4) Field number, sector number: indicate address data.
5) Track identification section: distinguish between lands and grooves Among the above, the sector mark, the synchronization pattern, and the address mark are fixed or identical in all sectors. Therefore, even if the beam spot 9 goes off the track center in these blocks, the beam spot 9 will still be partially on the pre-pits (having the same pattern) in the adjoining track, thereby reducing the liability of misdetecting these signals. By adopting wide pits for these pre-pits, the detection accuracy of these signals can be further enhanced.

Hereinafter, the principle of determining whether the beam spot 110 is tracing a land or a groove at a given moment will be described with respect to the optical disk according to the present example illustrated in FIG. 11.

Figures 14A, 14B:
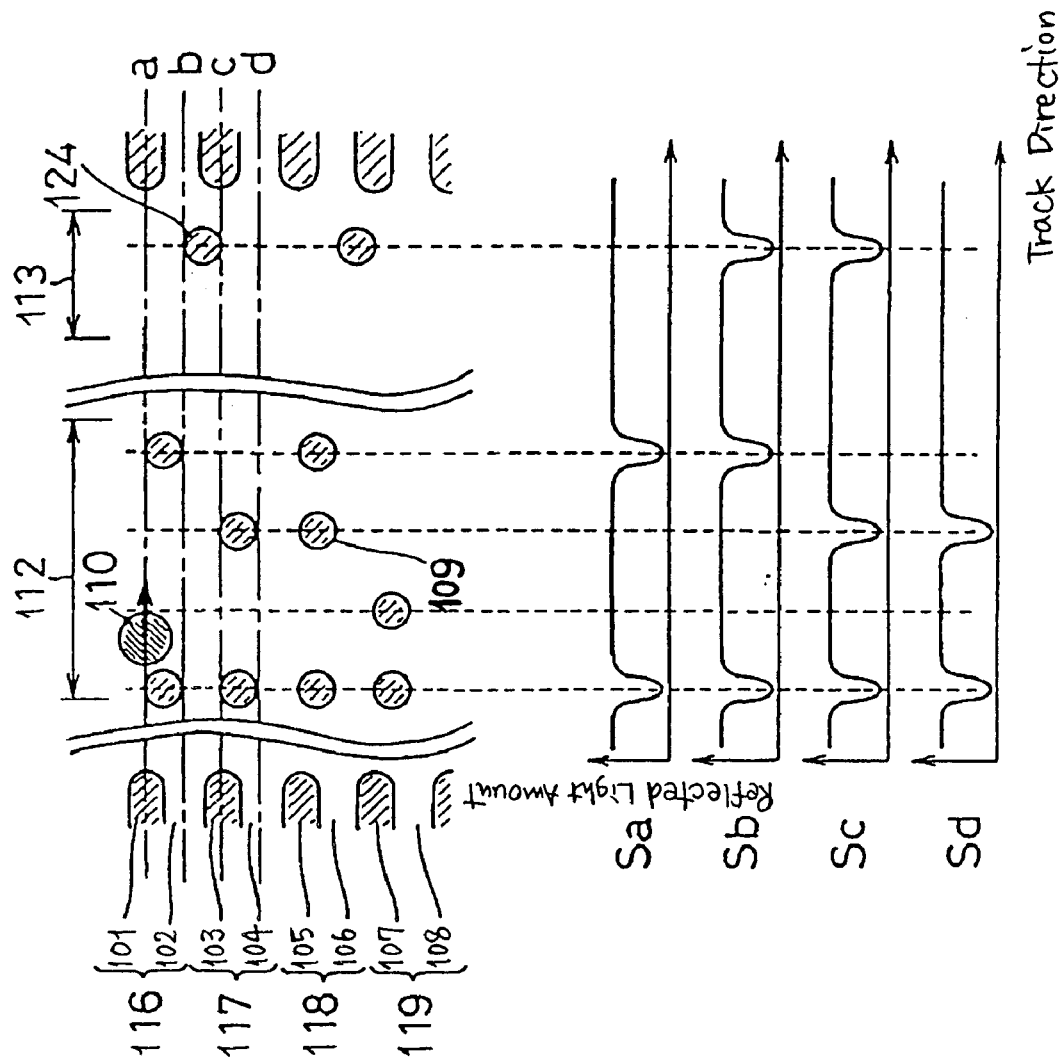
FIG. 14A is a magnified plan view showing an identification signal section of the optical disk shown in FIG. 11.
FIG. 14B is a waveform diagram describing a reproduced signal of the reflected light of a beam spot.

FIG. 14A is a magnified view showing the identification signal section of the optical disk according to the present example. FIG. 14B is a waveform diagram showing the amount of reflected light when a beam spot traces over the identification signal section. In FIG. 14A, reference numerals 101, 103, 105, 107, . . . etc., denote groves, while 102, 104, 106, 108, . . . etc., denote lands. Reference numerals 116, 117, 118, 119, . . . etc., denote fields. Reference numeral 109 denotes a pre-pit representing field numbers; 110 denotes a beam spot; 112 denotes a field number section; 113 denotes a track identification section; and 124 denotes a track identification pre-pit. These elements are identical with those indicated by like numerals in FIG. 11. Lines a and c are center lines of the grooves 101 and 103, respectively. Lines b and d are center lines of the lands 102 and 104, respectively. In FIG. 14B, Sa, Sb, Sc, and Sd illustrate the waveforms representing the reflected light amount when the beam spot 110 traces over the center lines a, b, c, and d, respectively, in the direction of the arrow in FIG. 14A.

In the field number section 112, the pre-pits 109 indicating field numbers are formed between the center lines a and b. Therefore, the waveforms Sa and Sb are identical. On the other hand, in the track identification section 113, the track identification pre-pit 124 is formed between the center lines b and c, so that only the waveform Sb has a peak. In other words, the track identification pre-pit 124 causes a peak only for the land track.

Similarly, in the field number section 112, the pre-pits 109 indicating field numbers are formed between the center lines c and d, so that the waveforms Sc and Sd are identical. However, in the track identification section 113, the track identification pre-pit 124 is formed between the center lines b and c, so that only the waveform Sc has a peak. In other words, the track identification pre-pit 124 causes a peak only for the groove track. Thus, the reproduction waveforms of the identification signal section 111 (FIG. 11) of two information tracks of the same field can be distinguished from each other.

Now, assuming that the field 116 has an odd field number and the field 117 has an even field number, it is possible to determine whether a currently traced track is a land or a groove as follows: Any information track in an odd-numbered field that shows a peak due to the track identification pre-pit 124 as the beam spot 110 traces the track identification section 113 is a land track, whereas any information track that does not show the above-mentioned peak is a groove track. In an even-numbered field, on the other hand, any information track that shows a peak due to the track identification pre-pit 124 as the beam spot 110 traces the track identification section 113 is a groove track, whereas any information track that does not show the above-mentioned peak is a land track. The track identification pre-pits 124 are provided for every other field so that the above principle is true of all the fields throughout the optical disk.

Thus, based on the information as to whether a given field number in the field number section 112 is an even number or an odd number and the presence/absence of a peak in the reflected light amount due to the track identification pre-pit 124, it can be determined whether a currently traced track is a land or a groove.

Next, an optical information recording/reproducing device capable of recording, reproducing or erasing information signals on the optical disk according to the present example will be described with reference to FIG. 15.

Figure 15:
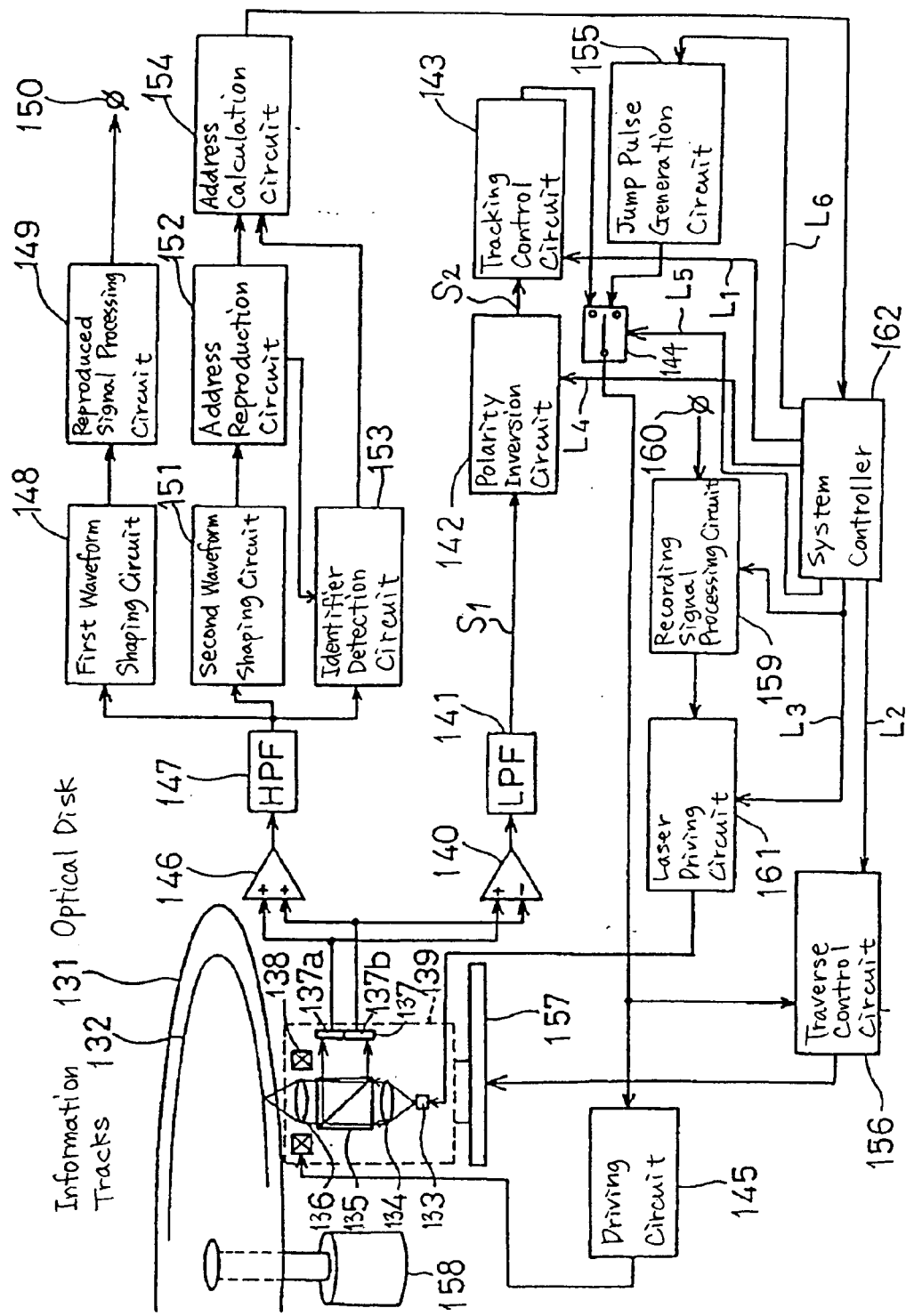
FIG. 15 is a block diagram showing the configuration of an optical information recording/reproduction device for the optical disk shown in FIG. 11.

FIG. 15 is a block diagram showing an exemplary configuration for the optical information recording/reproduction device of the present invention.

An optical disk 131 shown in FIG. 15 has the above-described structure, including "land" and "groove" information tracks 132. Information can be recorded on or reproduced from the optical disk 131 by using the optical information recording/reproducing device in FIG. 15.

First, the structure of an optical head 139 will be described. The optical head 139 includes a semiconductor laser element 133, a collimating lens 134 for collimating laser light emitted from the semiconductor laser element 133, a half mirror 135, an objective lens 136 for converging the collimated light led through the half mirror 135 onto an information surface of the optical disk 131, an optical detector 137 for receiving light reflected from the optical disk 131 via the objective lens 136 and the half mirror 135, and an actuator 138 supporting the objective lens 136. The optical detector 137 includes two light receiving portions 137a and 137b for generating a tracking error signal, the light receiving portions 137a and 137b defining two integral portions of the optical detector 137 divided in parallel to the direction of tracks on the optical disk 131. These elements of the optical head 139 are mounted on a head base (not shown).

The outputs of the optical pickup 139 (i.e., detected signals output from the light receiving portions 137a and 137b of the optical detector 137) are input to a differential amplifier 140 and an addition amplifier 146. The output of the differential amplifier 140 is input to a low-pass filter (LPF) 141. The LPF 141 receives a differential signal from the differential amplifier 140, and outputs a signal S1 to a polarity inversion circuit 142. The polarity inversion circuit 142 receives the signal S1 from the LPF 141 and a control signal L4 from a system controller 162 (described later), and outputs a signal S2 to a tracking control circuit 143.

On the other hand, the output of the addition amplifier 146 (an addition signal) is coupled to a high-pass filter (HPF) 147. The HPF 147 outputs high frequency components of the addition signal to a first waveform shaping circuit 148, a second waveform shaping circuit 151, and a identifier detection circuit 153. The first waveform shaping circuit 148 receives the high frequency components of the addition signal from the HPF 147 and outputs a digital signal to a reproduced signal processing circuit 149 (described later). The reproduced signal processing circuit 149 outputs a reproduced information signal to an output terminal 150. The second waveform shaping circuit 151 receives the high frequency components of the addition signal from the HPF 147 and outputs a digital signal to an address reproduction circuit 152 (described later). The address reproduction circuit 152 receives the digital signal from the second waveform shaping circuit 151, and outputs first address data to an address calculation circuit 154 (described later).

The identifier detection circuit 153 receives the high frequency components of the addition signal from the HPF 147 and outputs an identifier detection signal to the address calculation circuit 154.

The address calculation circuit 154 receives the first address data from the address reproduction circuit 152 and the identifier detection signal from the identifier detection circuit 153, and outputs second address data to the system controller 162.

The tracking control circuit 143 receives an output signal from the polarity inversion circuit 142 and a control signal L1 from the system controller 162, and outputs a tracking control signal to one of the two input terminals of a first selector 144. The first selector 144 receives the tracking control signal from the tracking control circuit 143, a driving pulse from a jump pulse generation circuit 155, and a control signal L5 from the system controller 162, so as to output a driving signal to a driving circuit 145 and a traverse control circuit 156.

The driving circuit 145 receives the driving signal from the first selector 144, and outputs a driving current to the actuator 138.

When the main information signal reproduced from recording marks and the identification signals reproduced from pre-pits have different reproduction amplitude levels, the first waveform shaping circuit 148 and the second waveform shaping circuit 151 are adapted to have different gains.

The jump pulse generation circuit 155 receives a control signal L6 from the system controller 162 and outputs a driving pulse to the first selector 144.

The traverse control circuit 156 receives a control signal L2 from the system controller 162 and the tracking control signal from the first selector 144, and outputs a driving current to a traverse motor 157.

The traverse motor 157 moves the optical head 139 along the radius direction of the optical disk 131. A spindle motor 158 rotates the optical disk 131.

A recording signal processing circuit 159 receives information signals (e.g., video signals and audio signals) via an external input terminal 160 and a control signal L3 from the system controller 162, and outputs a recording signal to a laser driving circuit 161 (described later). The laser driving circuit 161 receives the control signal L3 from the system controller 162 and the recording signal from the recording signal processing circuit 159, and outputs a driving current to the semiconductor laser element 133.

The system controller 162 receives the second address data from the address calculation circuit 154. The system controller 162 outputs the control signal L1 to the tracking control circuit 143, the control signal L2 to the traverse control circuit 156, the control signal L3 to the recording signal processing circuit 159 and the laser driving circuit 161, the control signal L4 to the polarity inversion circuit 142 and the address calculation circuit 154, the control signal L5 to the first selector 144, and the control signal L6 to the jump pulse generation circuit 155.

Next, the operations of the above-described optical information recording/reproduction device will be described with reference to FIG. 15.

First, the operation of reproducing information signals will be described.

The laser driving circuit 161 is placed in a reproduction mode by the control signal L3 from the system controller 162, and supplies a driving current to the semiconductor laser 133 so that the semiconductor laser 133 is driven to emit light at a predetermined intensity. The traverse control circuit 156 outputs a driving current to the traverse motor 157 in accordance with the control signal L2 from the system controller 162 so as to move the optical head 139 to a target track.

A laser beam emitted from the semiconductor laser 133 is collimated by the collimating lens 134, led through the beam splitter (half mirror) 135, and converged on the optical disk 131 by the objective lens 136.

A light beam reflected from the optical disk 131, carrying the information in the information tracks 132 through diffraction (i.e., a distribution of reflected light amount), is led through the objective lens 136 so as to be incident on the optical detector 137 due to the beam splitter 135.

The light receiving portions 137a and 137b of the optical detector 137 convert the intensity variation of the incident light beam into electric signals, and outputs the electric signals to the differential amplifier 140 and the addition amplifier 146. The differential amplifier 140 subjects the input currents to an I-V conversion and thereafter takes a difference therebetween, so as to output the difference as a differential signal to the LPF 141.

The LPF 141 extracts the low frequency components of the differential signal, and outputs the low frequency components as the signal S1 to the polarity inversion circuit 142. In accordance with the control signal L4 input from the system controller 162, the polarity inversion circuit 142 either allows the signal S1 to pass (as the signal S2) or inverts the polarities (i.e., plus or minus) thereof and outputs the result as the signal S2 to the tracking control circuit 143.

Herein, the signal S2 is a so-called "push-pull tracking error signal" which corresponds to the tracking error amount between the beam spot converged on the information surface of the optical disk 131 and the center of the target information track 132.

For the sake of convenience of description, it is assumed herein that the signal S1 is allowed to pass in the case where the target track (i.e., the track carrying information to be recorded or reproduced) is a groove and that the signal S1 is inverted in the case where the target track is a land.

The tracking control circuit 143 outputs a tracking control signal to the driving circuit 145 via the selector 144 in accordance with the level of the input signal S2. The driving circuit 145 supplies a driving current to the actuator 138 in accordance with the tracking control signal, whereby the position of the objective lens 136 is controlled along the direction across the information track 132. As a result, the beam spot properly scans the center of the information track 132.

The traverse control circuit 156 receives the tracking control signal, and drives the traverse motor 157 in accordance with the low frequency components of the tracking control signal so as to gradually move the optical head 139 along the radius direction of the optical disk 131 as the reproduction operation proceeds.

The selector 144 connects/disconnects the output of the jump pulse generation circuit 155 to/from the input of the driving circuit 145 in accordance with the control signal L5 from the system controller 162. The control signal L5 controls the selector 144 so as to couple the output of the jump pulse generation circuit 155 to the input of the driving circuit 145 only when moving the beam spot between information tracks, that is, when a "track jump" is made. Otherwise, the selector 144 couples the input of the driving circuit 145 to the tracking control circuit 143.

On the other hand, a focus control circuit (not shown) controls the position of the objective lens 136 along the direction of the optical axis so that the beam spot accurately focuses on the optical disk 131.

Once the beam spot is accurately positioned on the information track 132, the addition amplifier 146 subjects the output currents from the light receiving portions 137a and 137b to an I-V conversion, and thereafter adds the converted currents to output the result as an addition signal to the HPF 147.

The HPF 147 cuts off the unnecessary low frequency components of the addition signal, and allows the reproduced signals (i.e., the main information signal and the address signal) as signals having analog waveforms, which are output to the first waveform shaping circuit 148, the second waveform shaping circuit 151, and the identifier detection circuit 153.

The second waveform shaping circuit 151 subjects the address signal having an analog waveform to a data slice process using a second threshold value, thereby converting the address signal into a signal having a pulse waveform, which is output to the address reproduction circuit 152.

The address reproduction circuit 152 demodulates the input digital address signal, and outputs a field number and a sector number contained therein as the first address data to the address calculation circuit 154.

The identifier detection circuit 153 detects whether or not the reproduced waveform has a peak due to the track identification pre-pit as the beam spot 110 traces over the track identification section of the optical disk 131, and outputs the detection result as a digital signal having two levels, for example, as an identification detection signal to the address calculation circuit 154. Herein, it is assumed that the identification detection signal is at a Hi (High) level when the track identification pre-pit is detected, and a Lo (Low) level when no track identification pre-pits are detected. The track identification pre-pit can be detected by using a level comparator, a peak detection circuit, and the like as in the detection of other pre-pits. In the format structure shown in FIG. 13, the track identification section is located after the sector number, so that the track identification pre-pit can be detected by monitoring whether or not the reproduced waveform has a peak due to the track identification pre-pit after the lapse of a predetermined time from the reading the sector number.

Figure 16:
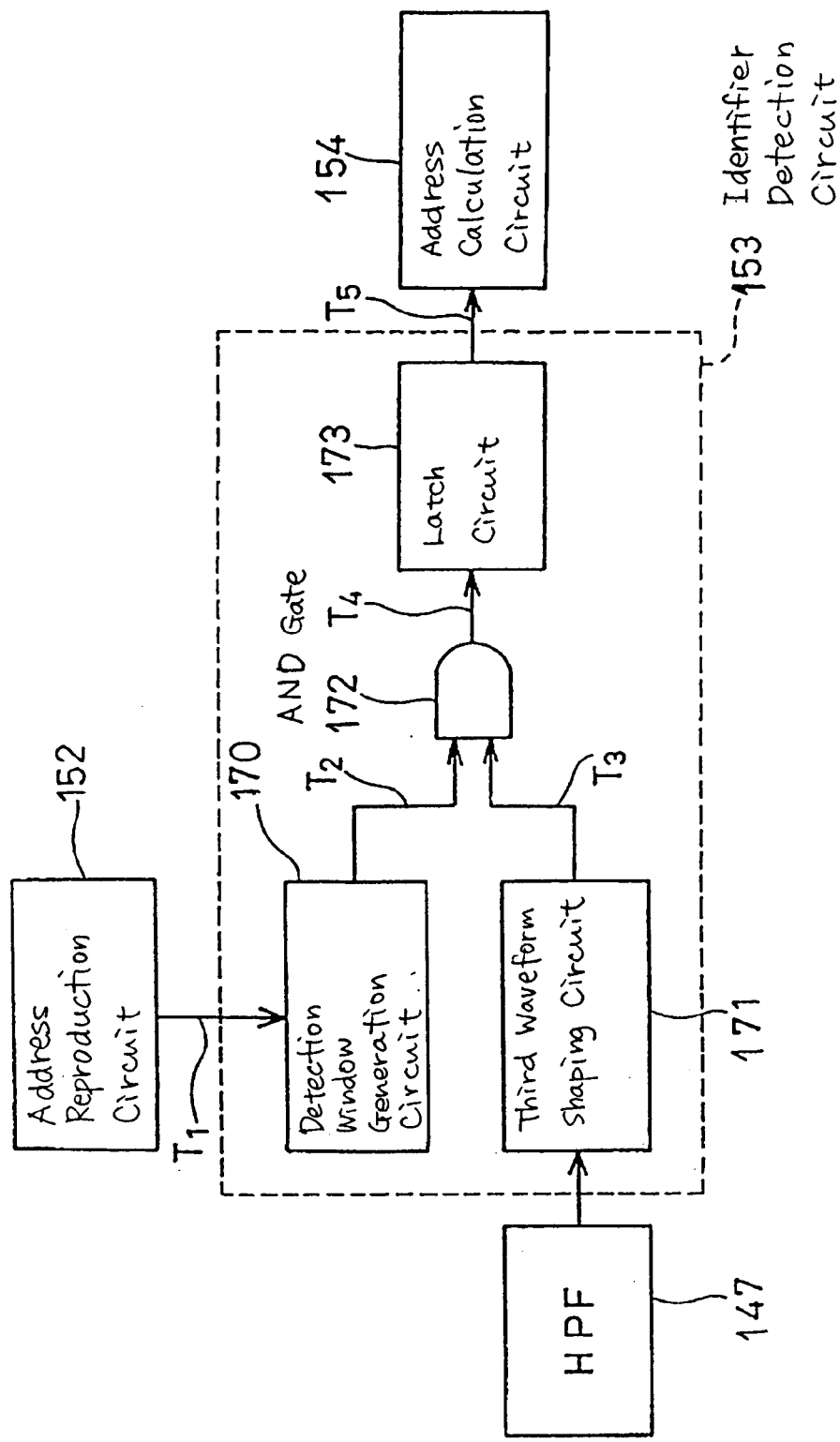
FIG. 16 is a block diagram showing the configuration of an identification detection circuit according to Example 5.
Figure 17:
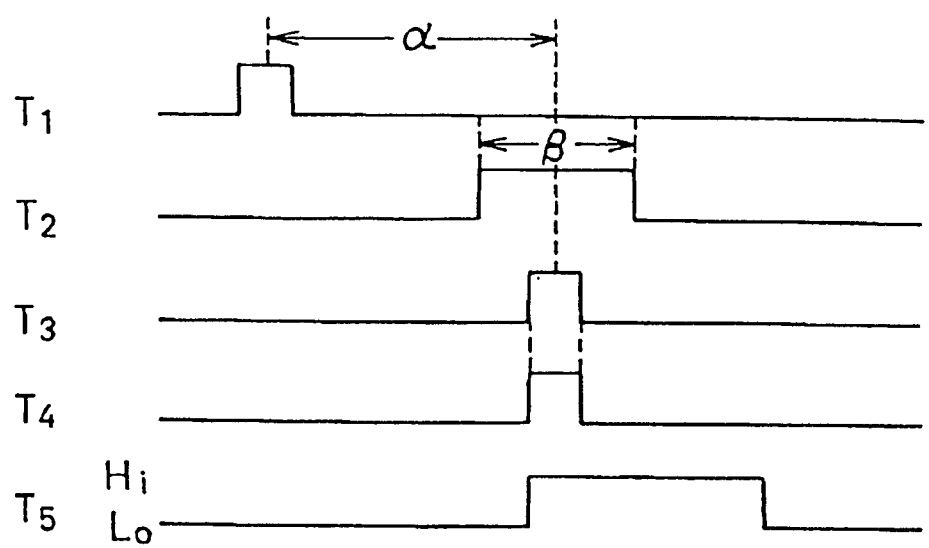
FIG. 17 is a timing diagram showing various signals in the identification detection circuit according to Example 5.

FIG. 16 is a block diagram showing the structure of the identifier detection circuit. Elements which also appear in FIG. 15 are indicated by the same reference numerals as used therein. FIG. 17 is a timing chart showing timing pulse signals T1 to T5. As shown in FIG. 16, a detection window generation circuit 170 receives the timing pulse T1 from the address reproduction circuit 152, indicating the beginning of the reading of the identification signal section. The detection window generation circuit 170 outputs, after a predetermined delay time α, the detection window signal T2 having a Hi level period of a predetermined detection window width β to an AND gate 172. The delay time α and the detection window width β are predetermined so that only the pulse due to the track identification pre-pit detected by the beam spot 110 falls within the Hi level period of the detection window signal T2 in FIG. 17, in view of factors such as the tracing speed of the beam spot 110, and the rotation variation of the spindle motor 158. On the other hand, a third waveform shaping circuit 171 subjects the reproduced signal from the HPF 147 having an analog waveform to a data slicing process using a third threshold value, and thereafter outputs the reproduced signal as the digital pulse T3 to the AND gate 172. The third threshold value is prescribed to be, for example, about half of the peak voltage so that the peak in the signal Sa or Sb due to the pre-pits 124 of the track identification section 113, obtained as the beam spot 110 traces over the track center in FIG. 14, becomes substantially detectable. The AND gate 172 performs a logical AND operation for the detection window signal T2 and the digital pulse T3, and outputs the result as the digital signal T4 to a latch circuit 173. Once the digital signal T4 shifts to the Hi level, the latch circuit 173 retains the Hi level of the digital signal T4 and outputs the signal as the identifier detection signal T5 to the address calculation circuit 154. The latch circuit 173 is reset by means of a timer or the like so that the latch circuit 173 does not retain or latch the input signal level any longer after the lapse of an amount of time sufficient for the calculation of the second address data in the address calculation circuit 154.

Although the timing of the generation of the timing pulse T1 was described to be based on the point of detecting the address mark, the reference point can alternatively be the detection of the sector mark, the field number, or the sector number.

Figure 18:
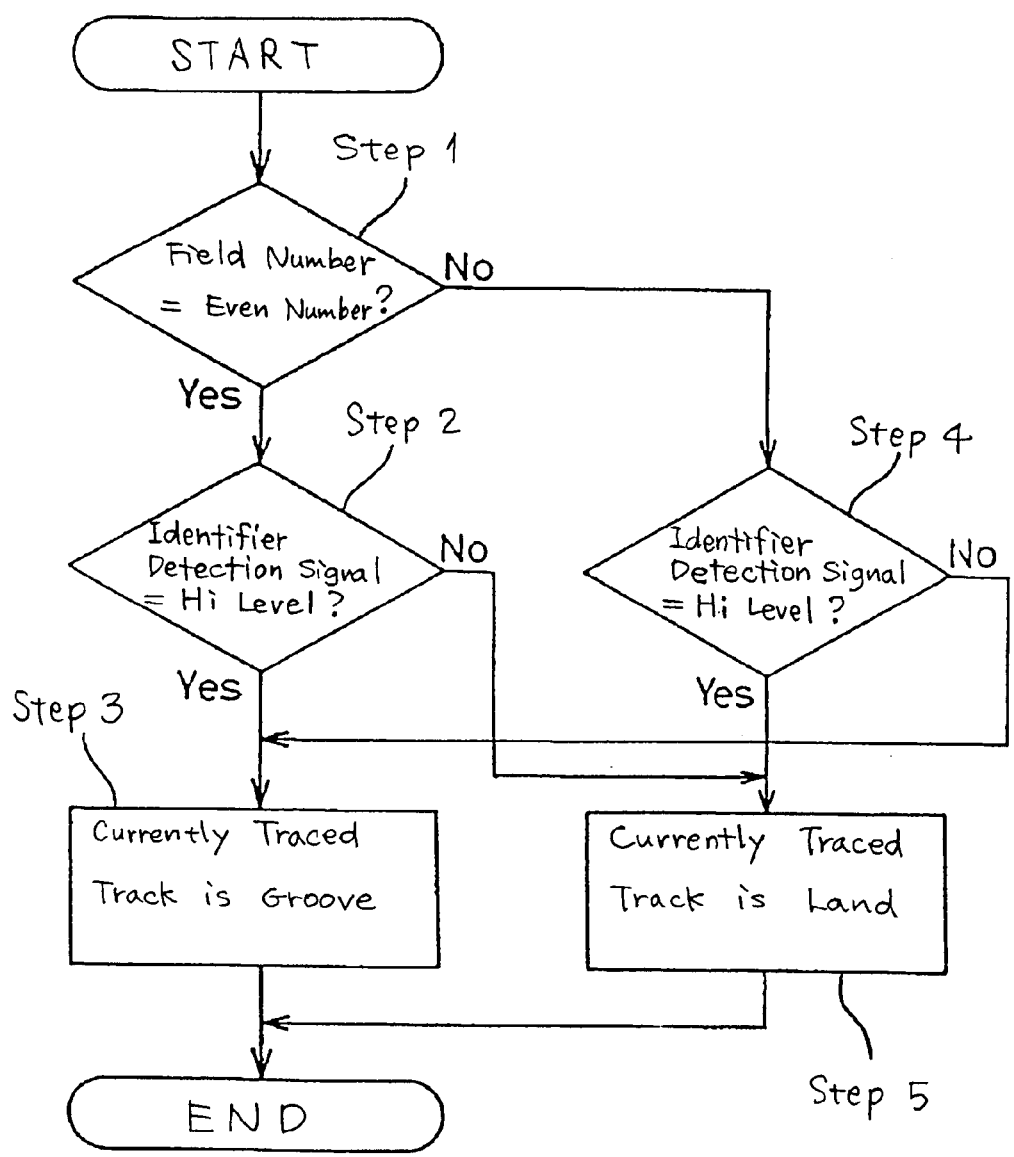
FIG. 18 is a flowchart showing an algorithm for determining whether a currently traced track is a land or a groove according to Example 5.

FIG. 18 shows an exemplary algorithm in the address calculation circuit 154 for determining whether the currently traced track is a land or a groove. At Step 1, it is determined whether the field number in the first address data is an even number or an odd number. If the field number is an even number, then the control proceeds to Step 2; if the field number is an odd number, then the control proceeds to Step 4. At Step 2, it is determined whether the identifier detection signal T5 is at the Hi level or the Lo level. If the identifier detection signal T5 is at the Hi level, then the control proceeds to Step 3; if the identifier detection signal T5 is at the Lo level, then the control proceeds to Step 5. At Step 4, too, it is determined whether the identifier detection signal T5 is at the Hi level or the Lo level. If the identifier detection signal T5 is at the Hi level, then the control proceeds to Step 5; if the identifier detection signal T5 is at the Lo level, then the control proceeds to Step 3. At Step 3, the currently traced track is determined to be a groove. At Step 5, the currently traced track is determined to be a land. Thus, the second data is obtained.

Referring back to FIG. 15, the address calculation circuit 154 determines whether the track currently scanned by the beam spot is a land or a groove based on the output level of the identifier detection signal T5 and on whether the field number of the first address data is odd or even. The address calculation circuit 154 outputs the result, along with the field number and the sector number, as the second address data to the system controller 162.

Based on the second address signal, the system controller 162 determines whether or not the beam spot is on a target address. If the beam spot is on the target address, the control signals L4 and L5 are maintained so that the beam spot proceeds to trace the main information signal section. While the beam spot traces the main information signal section, the first waveform shaping circuit 148 subjects the main information signal having an analog waveform (which is received via the optical detector 137, the addition amplifier 146, and the HPF 147) to a data slice process using a first threshold value, thereby converting the main information signal into a digital signal, which is output to the reproduced signal processing circuit 149.

The reproduced signal processing circuit 149 demodulates the input digital main information signal, and subjects the demodulated digital main information signal to appropriate processes (e.g., error correction) before it is output at the output terminal 150.

During recording, the system controller 162 informs the recording signal processing circuit 159 and the laser driving circuit 161 with the control signal L3 that the operation is in a recording mode.

The recording signal processing circuit 159 adds an error correction code, etc., to an audio signal, a video signal, computer data and the like which are input via the external input terminal 160, and outputs the signal as an encoded recording signal to the laser driving circuit 161. Once the laser driving circuit 161 is placed in a recording mode by the control signal L3, the laser driving circuit 161 modulates a driving current applied to the semiconductor laser 133 in accordance with the recording signal. As a result, the intensity of the beam spot 9 radiated onto the optical disk 131 changes in accordance with the recording signal, whereby recording pits are formed.

During reproduction, on the other hand, the control signal L3 places the laser driving circuit 161 in a reproduction mode, and the laser driving circuit 161 controls the driving current so that the semiconductor laser 133 emits light with a constant intensity which is lower than the light intensity during the recording mode.

While the above operations are performed, the spindle motor 158 rotates the optical disk 131 at a constant angular velocity.

Next, a seek operation, i.e., an operation of moving the beam spot 9 to a target address, will be described in more detail.

Once an address is designated from which to start recording/reproduction, the system controller 162 determines whether the sector of the designated address is included in a land track or a groove track, and outputs the judgment result as the control signal L4.

Herein, it is assumed that the control signal L4 is at a Lo level when the sector having the designated address is in a groove, and a Hi level when the sector of the designated address is in a land. Since the present example adopts the push-pull method as the method of tracking error detection, the polarity of the detected tracking error signal reverses depending on whether the track is a land or a groove. Accordingly, the polarity inversion circuit 142 inverts the polarities of the input signal if the start address is an address within a land, and the polarity inversion circuit 142 does not invert the polarities of the input signal if the start address is an address within a groove. The system controller 162 supplies the control signal L5 to the selector 144 so that the tracking control circuit 143 is selected as the input source of the driving circuit 145. At this time, the tracking control circuit 143 is controlled by the control signal L1 not to output a tracking control signal.

Next, the control signal L2 is sent to the traverse control circuit 156 so as to drive the traverse motor 157 for a "coarse" seek movement. This "coarse" seek movement is made by previously calculating the number of tracks present between the current address (i.e., the address before the movement) and the target address, based on the values of the current and target addresses, and comparing the pre-calculated number with the number of tracks traversed during the movement (which is derived from the tracking error signal).

Then, the control signal L1 causes the tracking control circuit 143 to output a tracking control signal to the driving circuit 145 and the traverse control circuit 156 via the selector 144, so that the beam spot 9 roughly traces a land or a groove. Once a tracking lock-in procedure is complete, address data from the identification signal section is reproduced. That is, the first address data is input to the address calculation circuit 154 via the optical detector 137, the addition amplifier 146, the HPF 147, the second waveform shaping circuit 151, and the address reproduction circuit 152.

The address calculation circuit 154 calculates the second address data based on the input first address data and the identifier detection signal from the identifier detection circuit 153, and outputs the second address data to the system controller 162.

The system controller 162 compares the second address data against the target address value. If the second address data does not coincide with the target address value, the system controller 162 causes the selector 144 to couple the output of the jump pulse generation circuit 155 with the input of the driving circuit 145 based on the control signal L5. In addition, the system controller 162 causes the traverse control circuit 156 not to output a driving signal to the traverse motor 157 by using the control signal L2. Subsequently, the system controller 162 causes the jump pulse generation circuit 155 to output a driving pulse to driving circuit 145 based on the control signal L6, the driving pulse corresponding to the above-mentioned difference in field numbers.

The driving circuit 145 supplies a driving current corresponding to the driving pulse to the actuator 138, and causes the beam spot 9 to make a "track jump" by a designated number of tracks. Herein, a "track jump" is defined as a movement of the beam spot from a groove to a next groove, or from a land to a next land. Once the track jump by the designated number of tracks is complete, then a tracking lock-in procedure is performed, and after the beam spot 9 has arrived at the target sector due to the rotation of the optical disk 131, the recording/reproduction of information signals is started in this sector.

Although only one track identification pre-pit is provided in the optical disk of the present example, it is also applicable to provide a plurality of track identification pre-pits, which would reduce the liability of misdetection in track identification, leading to a more reliable detection.

In the case where a plurality of track identification pre-pits are formed, the liability of misdetection in track identification can be further reduced by ensuring that the track identification pre-pits have a pattern which does not appear in any other signals of the identification signal section.

EXAMPLE 6

Figure 19:
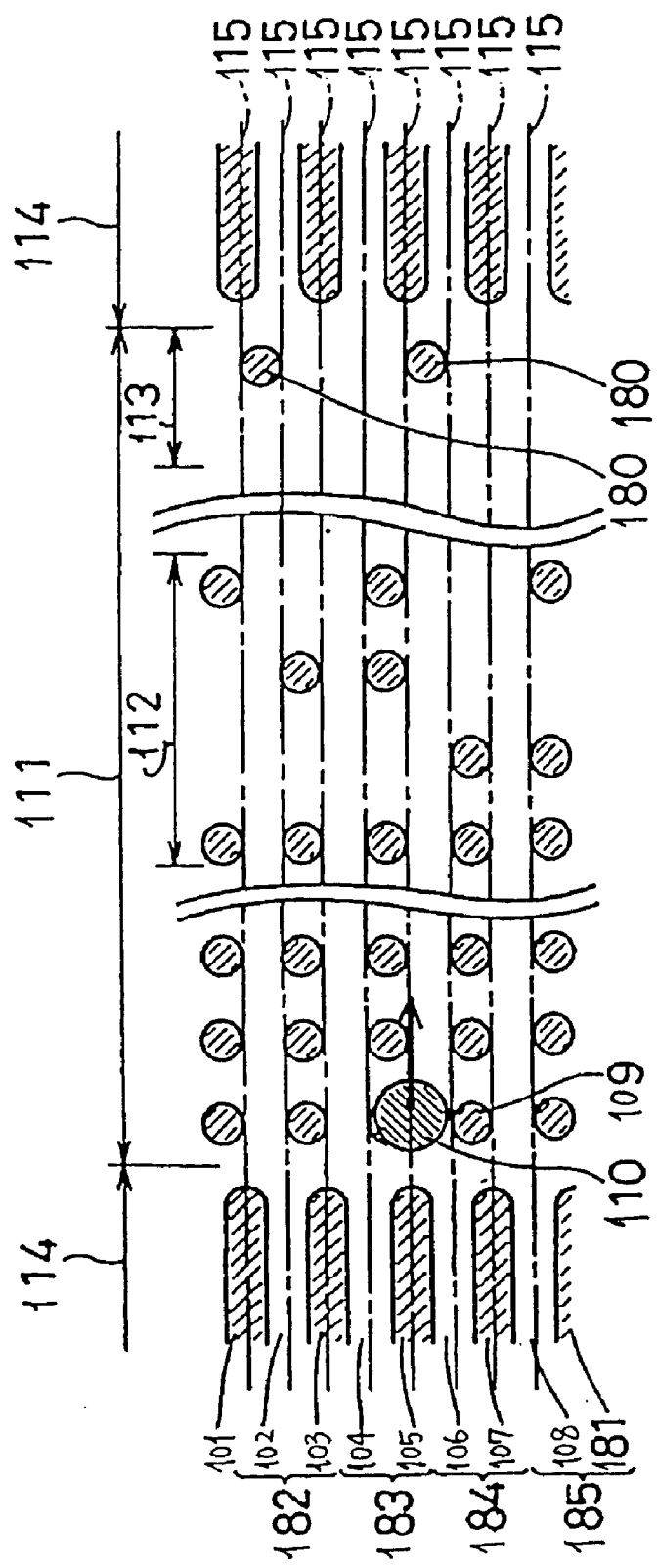
FIG. 19 is a magnified plan view showing an essential portion of the optical disk according to Example 6 of the present invention.

FIG. 19 is a magnified plan view showing an essential portion of an optical information recording medium according to Example 6 of the invention. In FIG. 19, reference numerals 101, 103, 105, 107, . . . etc., denote grooves, while 102, 104, 106, 108, . . . etc., denote lands. Reference numeral 109 denotes a pre-pit; 110 denotes a beam spot; 111 denotes an identification signal section; 112 denotes a field number section; 113 denotes a track identification section; and 114 denotes a main information signal section. These elements are identical with those indicated by like numerals in FIG. 11 illustrating Example 5. Reference numeral 180 denotes a track identification pre-pit. Track identification pre-pits are arranged in the same manner as the track identification pre-pits 124 in the track identification section 113 shown in FIG. 11. Reference numeral 181 denotes a groove; 182 denotes a field consisting of the land 102 and the groove 103; 183 denotes a field consisting of the land 104 and the groove 105; 184 denotes a field consisting of the land 106 and the groove 107; 185 denotes a field consisting of the land 108 and the groove 181. In the present example, the pre-pits 109 in the identification signal section 111 are all shifted along the radius direction of the optical disk by half a groove pitch. Otherwise the optical disk has the same configuration as that shown in FIG. 11. In the present example, as well as Example 5, the lands and the grooves can be distinguished based on the information as to whether a given field number is an even number or an odd number and the presence/absence of the track identification pre-pit 180.

EXAMPLE 7

Figure 20:
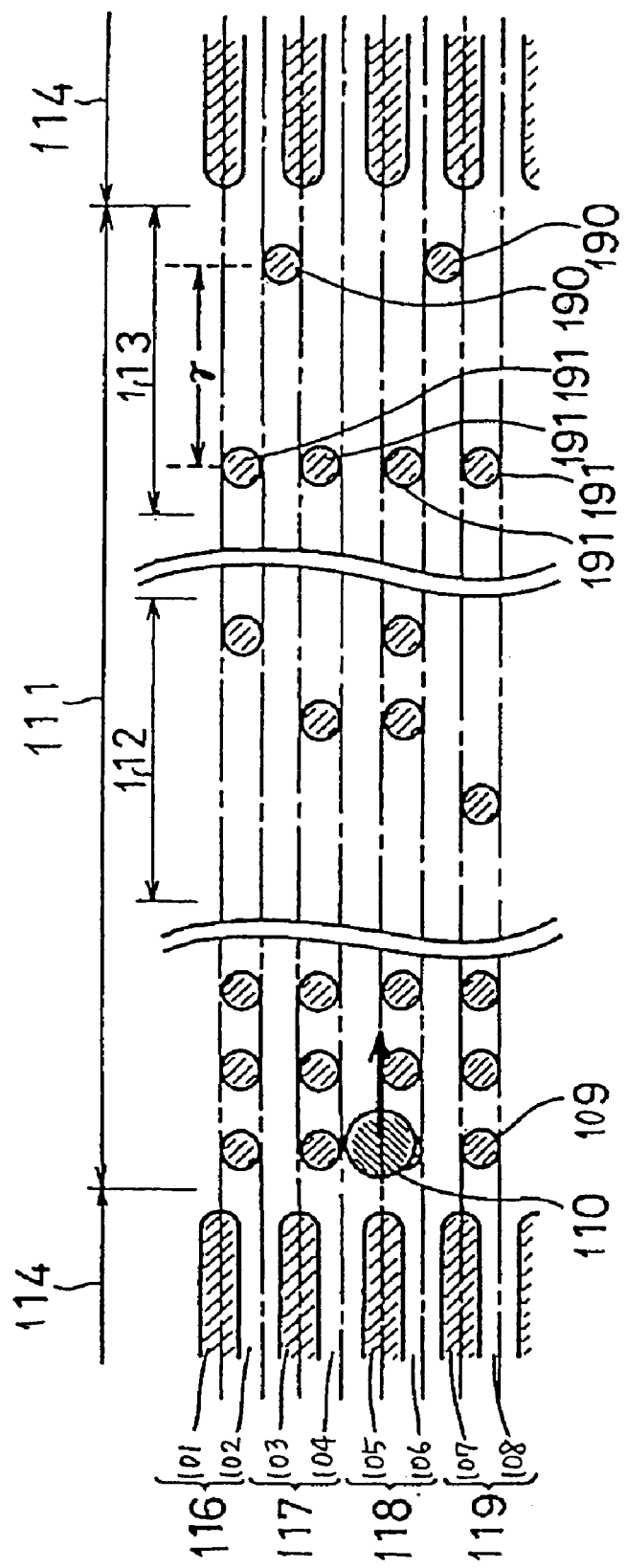
FIG. 20 is a magnified plan view showing an essential portion of the optical disk according to Example 7 of the present invention.

FIG. 20 is a magnified plan view showing an essential portion of an optical information recording medium according to Example 7 of the invention. In FIG. 20, reference numerals 101, 103, 105, 107, ... etc., denote grooves, while 102, 104, 106, 108, ... etc., denote lands. Reference numeral 109 denotes a pre-pit; 110 denotes a beam spot; 111 denotes an identification signal section; 112 denotes a field number section; 113 denotes a track identification section; and 114 denotes a main information signal section. These elements are identical with those indicated by like numerals in FIG. 11 illustrating Example 5. Reference numeral 190 denotes a track identification pre-pit. Track identification pre-pits are arranged in the same manner as the track identification pre-pits 124 in the track identification section 113 shown in FIG. 11. Reference numeral 191 denotes a pre-pit for the generation of timing pulses. The pre-pits 191 are formed on the same line as the pre-pits 109 of the field number section 112 with a period equal to the groove pitch. The pre-pits 191 for the generation of timing pulses are located in front of the track identification pre-pits 190 at a distance of γ. Since the pre-pits 191 are on the same line as the pre-pits 109 of the field number section 112, they can be detected regardless of whether the beam spot 110 is tracing on a land or a groove. Therefore, the detected signals of the pre-pits 191 can be used as the timing pulse Ti described in Example 5.

EXAMPLE 8

Figure 21:
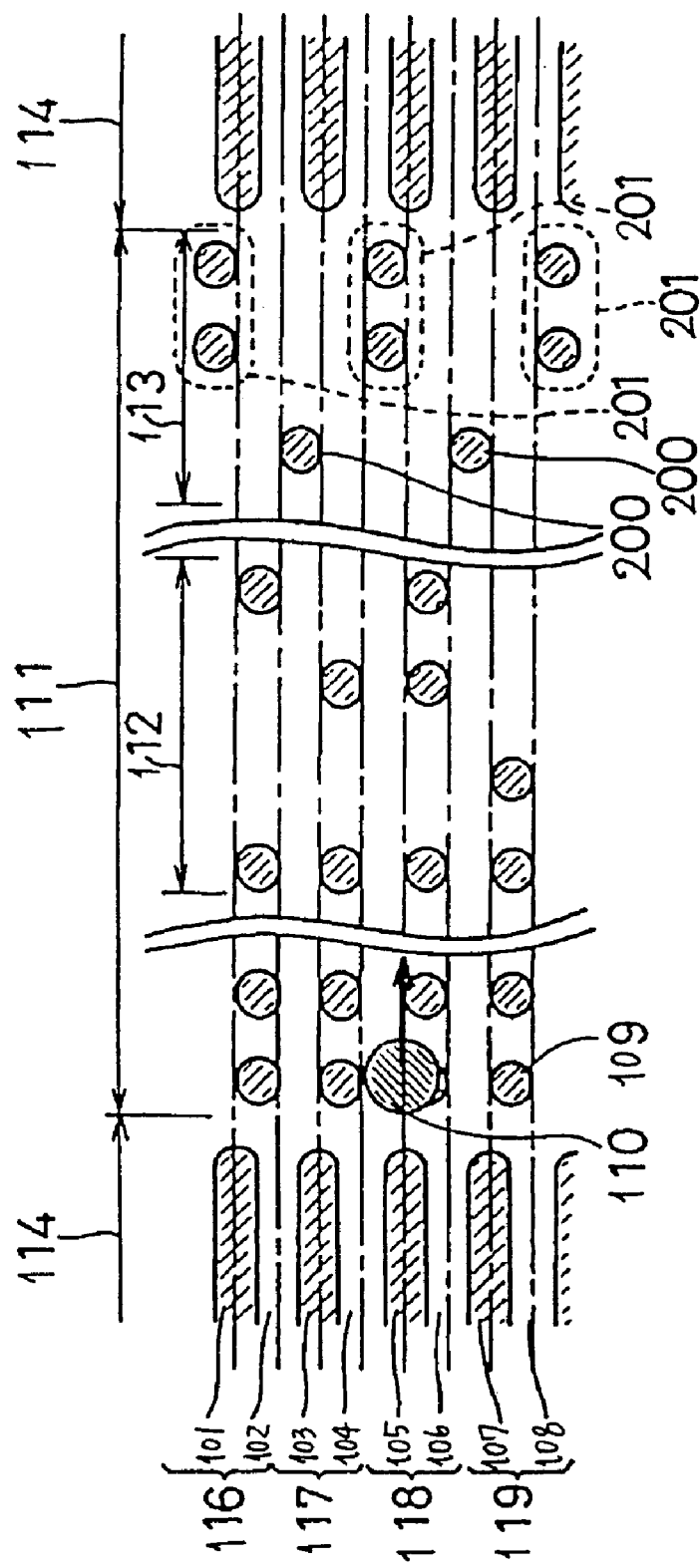
FIG. 21 is a magnified plan view showing an essential portion of the optical disk according to Example 8 of the present invention.

FIG. 21 is a magnified plan view showing an essential portion of an optical information recording medium according to Example 8 of the invention. In FIG. 21, reference numerals 101, 103, 105, 107, ... etc., denote grooves, while 102, 104, 106, 108, ... etc., denote lands. Reference numeral 109 denotes a pre-pit; 110 denotes a beam spot; 111 denotes an identification signal section; 112 denotes a field number section; 113 denotes a track identification section; and 114 denotes a main information signal section. These elements are identical with those indicated by like numerals in FIG. 11 illustrating Example 5. Reference numeral 200 denotes a first track identification pre-pit. One pre-pit 200 is formed for every other field so as to be located between the extensions of the pre-pit arrays in the field number section 112. Reference numeral 201 denotes a second track identification pre-pit located behind (along the longitudinal direction of the tracks) the first identification pre-pits 200. A pair of pre-pits 201 are formed for every other field so as to be located where the first identification pre-pits 200 are not located.

Figures 22A, 22B:
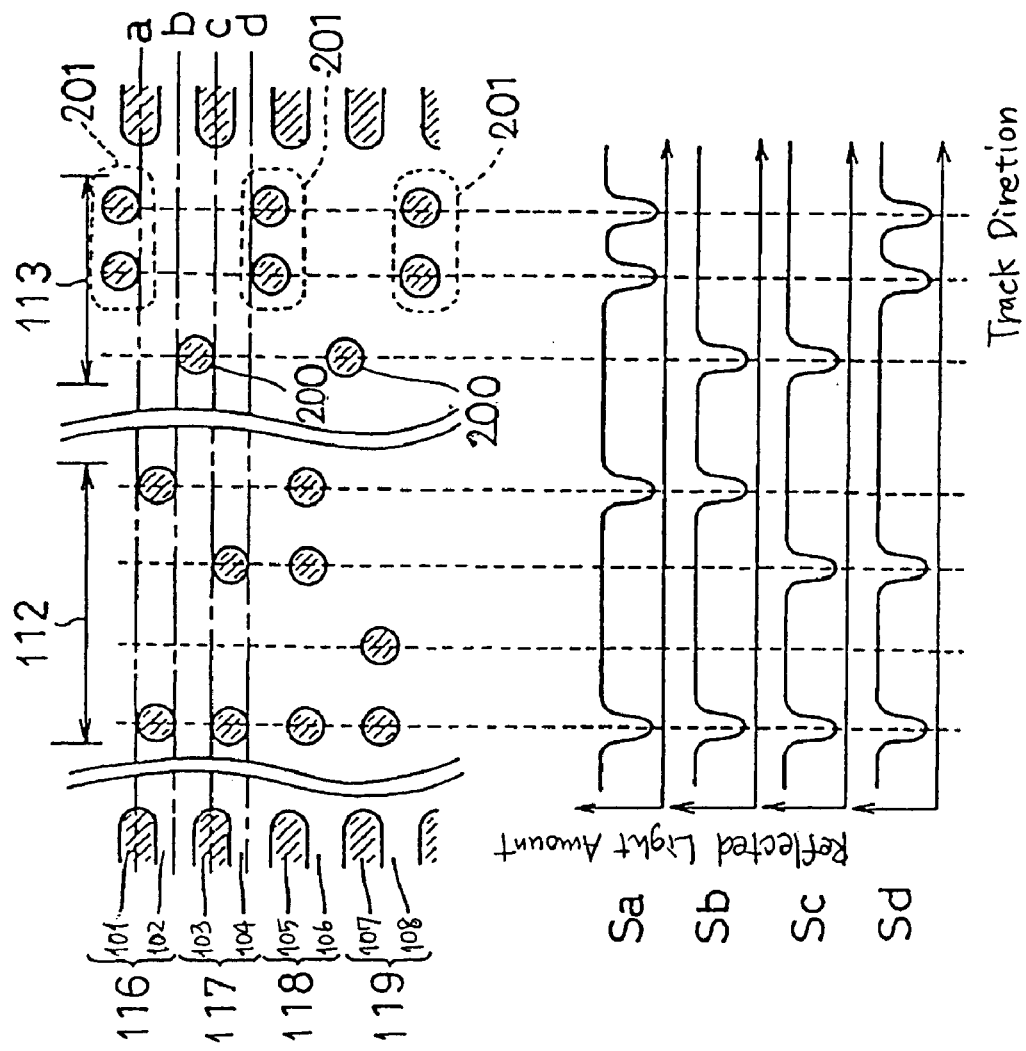
FIG. 22A is a magnified plan view showing an identification signal section of the optical disk shown in FIG. 21.
FIG. 22B is a waveform diagram describing a reproduced signal of the reflected light of a beam spot.

FIG. 22A is a magnified view showing the identification number section of the optical disk of the present example. FIG. 22B is a waveform diagram showing the reflected light amount obtained as the beam spot 110 traces over the identification signal section. In FIG. 22A, lines a and c are center lines of the grooves 101 and 103, respectively, while lines b and d are center lines of the lands 102 and 104, respectively. In FIG. 22B, Sa, Sb, Sc, and Sd illustrate the waveforms representing the reflected light amount when the beam spot 110 traces over the center lines a, b, c, and d, respectively, in the direction of the arrow in FIG. 22A.

In the field number section 112, the pre-pits 109 indicating field numbers are formed between the center lines a and b. Therefore, the waveforms Sa and Sb are identical. On the other hand, in the track identification section 113, two second track identification pre-pits 201 are formed next to the center line a and one first track identification pre-pit 200 is formed next to the center line b. Therefore, Sa has two peaks in the track identification section 113, whereas Sb has only one peak in the track identification section 113.

Similarly, in the track identification section 113, two second track identification pre-pits 201 are formed next to the center line d and one first track identification pre-pit 200 is formed next to the center line c. Therefore, Sc has one peak in the track identification section 113, whereas Sd has two peaks in the track identification section 113.

Now, assuming that the field 116 has an odd field number and the field 117 has an even field number, as in Example 5, it is possible to determine whether a currently traced track is a land or a groove as follows: Any information track in an odd-numbered field that shows one peak in the track identification section 113 is a land track, whereas any information track that shows two peaks in the track identification section 113 is a groove track. In an even-numbered field, on the other hand, any information track in an odd-numbered field that shows one peak in the track identification section 113 is a groove track, whereas any information track that shows two peaks in the track identification section 113 is a land track.

Thus, based on the information as to whether a given field number in the field number section 112 is an even number or an odd number and the number of peaks in the reflected light amount in the track identification section 113, it can be determined whether a currently traced track is a land or a groove.

In the present example, the first and second track identification pre-pits 200 and 201 cause such peaks regardless of whether the field number is an even number or an odd number and whether the track is a land or a groove. Therefore, lands and grooves can be accurately determined without misdetection.

Although the pre-pits of the identification signal section 111 are provided between the center lines of lands and grooves in the optical disk of Examples 5 to 8, the pre-pits of the identification signal section 111 do not have to be provided exactly in the middle between the center lines of lands and grooves, but may be slightly shifted toward the groove or the land. In such cases, the amplitude of the reproduced waveforms of the identification signals may vary depending on whether they correspond to a land or a groove, but an appropriate waveform shaping can be achieved in either case, by switching between two levels of threshold values (i.e., one for the lands and the other for the grooves) in the data slicing performed in the second waveform shaping circuit 151.

For example, in the case where the disk substrate has been produced in such a manner that the pre-pits are shifted toward a land from the exact middle between the land and the groove, the amplitudes of the reproduced identification signals become larger in the lands than in the grooves. Therefore, it is desirable to accordingly increase the threshold value for the lands.

Such an optical disk results in a smaller disturbance in the push-pull signal than in the case where the pre-pits in the identification signal section 111 are disposed in the exact middle between a land and a groove, and therefore contributes to a more stable tracking control.

As for the optical disk substrate, a substrate made of glass, polycarbonate, acryl, or the like can be used. An acryl substrate is preferable for the following reason: As the present inventors described in Japanese Laid-Open Patent Publication No. 6-338064, there is a major problem of diffusion of heat to adjoining tracks during the recording of information in both lands and grooves of a rewritable recording medium. Such heat diffusion can be minimized by adopting a steep groove edge so that the recording layer is disrupted or extremely thin at the edge portion. Such grooves with steep edges are relatively easy to produce from acryl, due to its good transcribability.

Although the depth of the pre-pits was described to be equal to the depth of the grooves in Examples 5 to 8, it is also applicable to adopt a different depth for the pre-pits. By prescribing the pre-pit depth to be λ/4, in particular, the beam spot can acquire a large diffraction effect so that the degree of modulation of identification signals and the like can be increased.

Although field numbers were assigned to pairs of lands and grooves in the identification signal section of Examples 5 to 8, it is also applicable to universally number all tracks, without distinguishing between lands and grooves. Since the pre-pits in the identification signal section correspond to every other track, the track numbers to be formed as the pre-pits in the identification signal section are either all numbers or all even numbers. Thus, depending on the determination in the track identification section as to whether the currently traced track is a land or a groove, the track numbers can be properly known by adding one to the track number obtained from the reproduced pre-pits for a groove, and not adding one to the track number obtained from the reproduced pre-pits for a land.

In the optical disks of Examples 5 to 8, lands and grooves are used as information tracks, and each pair consisting of a land and a groove adjoining each other is defined as one information field. However, any other configuration can be adopted as long as the track pitch of the main information signal section is half of the track pitch of the identification signal section (consisting of pre-pits). For example, Examples 5 to 8 are applicable to an magnetooptical disk utilizing magnetic super-resolution effects.

Thus, according to the present invention, an optical disk with an improved recording density can be provided. For example, it becomes possible to record about the same amount of video information of a laser disk on a disk of the size of a compact disk (CD), thereby allowing a reduction in the size of the optical information recording/reproduction device. For example, by employing the above-mentioned optical information recording/reproduction device in place of CD-ROM reproduction devices, which have recently become prevalent in the field of personal computers, it becomes possible to record and reproduce high-quality video data (which requires a large recording capacity) on the optical disk of any of Examples 1 to 8. Thus, the portability of large-capacity information recording media can be improved.

The optical disks used in Examples 1 to 8 typically have the following dimensions:

groove pitch: 1.48 μm track pitch: 0.74 μm groove depth: about 60 to 80 nm pit depth: about 60 to 80 nm groove width (land width): 0.6 to 0.7 μm width of pre-pits in the identification signal section: 0.5 to 0.7 μm minimum value of length of pre-pits in the identification signal section: about 0.6 μm laser light wavelength: 650 nm numerical aperture (NA) of objective lens: 0.6

It will be appreciated that the present invention is not limited to the above-mentioned dimensions.

Thus, in accordance with the optical information recording medium and the optical information recording/reproduction device of the present invention, the residual offset in tracking control is cancelled based on wobble pits in a servo region before a beam spot arrives at an identification signal section consisting of pre-pits disposed off the centerlines of lands and grooves. Therefore, the beam spot can accurately trace on the track centers, enabling stable detection of identification signals.

Moreover, according to the present invention, it can be determined which of the two kinds of information tracks the beam spot is currently tracing on, by detecting the field number and the track identifier formed in the form of pre-pits on a disk substrate. As a result, accurate locational information can be obtained in an optical information recording medium including information tracks with a track pitch narrower than the minimum track pitch of pre-pits. Thus, an optical information recording medium with an increased recording density can be provided.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A system, comprising:

an optical information recording medium comprising at least one groove track having a track center and allowing information to be recorded on or reproduced from the groove track; and an apparatus for illuminating the optical information medium with an optical beam to form a beam spot thereon, the apparatus comprising a tracking controller for controlling a tracking of the optical beam with respect to the groove track, wherein:

the groove track includes wobble grooves with respect to the track center, and shifted pits with respect to the track center, the wobble grooves and the shifted pits being positioned immediately adjacent to each other along the groove track, and the length of one wobble of the wobble grooves is longer than the diameter of the beam spot, and is shorter than the minimum length followable by the tracking controller.

* * * * *